United States Patent
Liu et al.

(10) Patent No.: US 12,072,402 B2
(45) Date of Patent: Aug. 27, 2024

(54) MULTIPHOTON MAGNETIC RESONANCE IMAGING

(71) Applicant: THE REGENTS OF THE UNIVERSITY OF CALIFORNIA, Oakland, CA (US)

(72) Inventors: Chunlei Liu, Orinda, CA (US); Victor Han, Berkeley, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 282 days.

(21) Appl. No.: 17/664,799

(22) Filed: May 24, 2022

(65) Prior Publication Data
US 2022/0334203 A1    Oct. 20, 2022

Related U.S. Application Data

(63) Continuation of application No. PCT/US2020/063410, filed on Dec. 4, 2020.
(Continued)

(51) Int. Cl.
*G01R 33/389*  (2006.01)
*A61B 5/055*   (2006.01)
(Continued)

(52) U.S. Cl.
CPC ............. *G01R 33/389* (2013.01); *A61B 5/055* (2013.01); *G01R 33/3815* (2013.01); *G01R 33/3852* (2013.01)

(58) Field of Classification Search
CPC ............... A61B 5/055; G01R 33/3515; G01R 33/3852; G01R 33/389
See application file for complete search history.

(56) References Cited

U.S. PATENT DOCUMENTS 4,972,147 A * 11/1990 Van Vaals .......... G01R 33/4833
                                                    324/309
11,215,805 B2 * 1/2022 Oldham ............. A61B 1/00172
(Continued)

OTHER PUBLICATIONS

Han, Victor et al., "Multiphoton magnetic resonance in imaging: A classical description and implementation", Magnetic Resonance in Medicine, 84, pp. 1184-1197.
(Continued)

*Primary Examiner* — Gregory H Curran
(74) *Attorney, Agent, or Firm* — O'BANION & RITCHEY LLP; John P. O'Banion

(57) ABSTRACT

Systems and methods are provided for multiphotonic magnetic resonance imaging. The system uses one or more ($B_{1,z}$) RF coils or oscillating gradients oriented along the z-axis to provide multiphoton resonances. The $B_{1,z}$ coils can be implemented as planar coils or solenoids. With the additional coils, standard slice-selective pulse sequences have all standard excitations replaced with multiphoton excitations that excite extra resonances. In vivo imaging using multiphoton excitation has signal to noise ratios comparable to single-photon excitations when similar pulse sequences are used. Since excitation is not bound to the Larmor frequency, new RF pulse sequences can be designed with imaging methods patterned after single-photon excitation concepts.

23 Claims, 6 Drawing Sheets

Related U.S. Application Data

(60) Provisional application No. 62/943,354, filed on Dec. 4, 2019.

(51) Int. Cl.
   *G01R 33/3815*   (2006.01)
   *G01R 33/385*    (2006.01)

(56) References Cited

U.S. PATENT DOCUMENTS

| | | |
|---|---|---|
| 11,491,224 B2 * | 11/2022 | Wong .................... A61K 45/06 |
| 2005/0065431 A1 | 3/2005 | Reiderman |
| 2011/0089942 A1 | 4/2011 | Goodwill |
| 2012/0056620 A1 | 3/2012 | Feinberg |
| 2013/0211391 A1 | 8/2013 | Benyakar |
| 2013/0320978 A1 | 12/2013 | Nasiraei Moghaddam |
| 2014/0225612 A1 | 8/2014 | Polimeni |
| 2019/0146049 A1 | 5/2019 | Koch |

OTHER PUBLICATIONS

ISA/US, United States Patent and Trademark Office (USPTO), International Search Report and Written Opinion issued Mar. 3, 2021, related PCT international application No. PCT/US2020/063410, pp. 1-7, with claims searched, pp. 8-12.

* cited by examiner

Lab Frame

Two Absorb

One Photon

Absorb and Emit

MULTIPHOTON MAGNETIC RESONANCE IMAGING

CROSS-REFERENCE TO RELATED APPLICATIONS

This application claims priority to, and is a 35 U.S.C. § 111(a) continuation of, PCT international application number PCT/US2020/063410 filed on Dec. 4, 2020, incorporated herein by reference in its entirety, which claims priority to, and the benefit of, U.S. provisional patent application Ser. No. 62/943,354 filed on Dec. 4, 2019, incorporated herein by reference in its entirety. Priority is claimed to each of the foregoing applications.

The above-referenced PCT international application was published as PCT International Publication No. WO 2021/113711 A1 on Jun. 10, 2021, which publication is incorporated herein by reference in its entirety.

STATEMENT REGARDING FEDERALLY SPONSORED RESEARCH OR DEVELOPMENT

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

This technology pertains generally to magnetic resonance imaging techniques and more particularly to systems and methods for multiphoton magnetic resonance imaging.

2. Background

Modern magnetic resonance imaging (MRI) systems utilize strong homogeneous magnetic fields, radio frequency electromagnetic pulses and the spin properties of certain atomic nuclei to create images of a subject. Commercially available MRI systems have several common well understood features and fundamental processes as well as known limitations inherent in the system.

When a test subject is exposed to a uniform magnetic polarizing field ($B_0$), individual magnetic moments of the spins of the nuclei attempt to align with the polarizing field and the resultant energy levels of the individual spins are dependent on the strength of the magnetic field. However, individual spins can be induced to flip into the opposite spin or resonate with the application of the right amount of additional energy. This resonance occurs when a radio-frequency pulse at the Larmor frequency is applied to the subject. In the presence of an excitation RF field ($B_1$), the magnetization performs a precessional motion about the z-axis called Free Induction Decay (FID) and the signal emitted by the excited spins after cessation of the excitation pulse can be received and processed to produce and image.

Conventional MRI systems known in the art are based on single-photon excitation. That is, for each nuclear spin, a single photon accompanies the transition between energy states. This photon must resonate near the Larmor frequency. Standard single-photon excitation occurs when the RF field ($B_1$) is polarized in the xy-plane, perpendicular to the main magnetic field $B_0$.

The RF excitation pulse has the same frequency as the processional frequency of the protons to transfer energy to the protons to disturb the proton spins out of alignment with the $B_0$ field. The RF pulse also causes the proton spins to move in the same direction simultaneously (i.e. in phase). Therefore, RF pulses are set at the Larmor frequency. The longitudinal and transverse components of the resulting magnetization begin to relax at the end of the RF excitation pulse until the magnetization returns to a state of equilibrium. The transverse relaxation emits signals that are received using a set of receiver coils. In some systems, the RF coils perform the dual role of transmission and reception.

Normally, strong RF pulses are needed to generate transverse magnetization that is later detected as a weak MRI signal by the receiver antenna coils. These standard pulses may cause too much patient heating, may not have enough spatial encoding ability, and may limit flexibility by limiting or precluding the acquisition of information regarding certain properties of a patient or sample. Accordingly, there is a need for improved MRI imaging devices and methods that do not have the deficiencies of conventional single photon imaging systems.

BRIEF SUMMARY

Systems and methods are provided for multiphoton MRI imaging that have an adaptable framework that permits the development of new pulses and imaging approaches as well as the use of pulses and schemes already explored with standard single-photon excitation. Standard single-photon excitation occurs when the RF field ($B_1$) is polarized in the xy-plane, perpendicular to the main magnetic field $B_0$. Multiphoton effects occur when more RF fields are added along the z-axis, parallel to the main magnetic field $B_0$. The z-direction magnetic field in multiphoton excitation can be implemented in a variety of ways. In one embodiment, at least one additional RF Coil producing a magnetic field oriented in the z-direction is incorporated into a conventional MRI scanner system.

With a constant z-photon frequency, it is observed that slice selective xy-RF pulses (e.g. sincgauss pulses) simply act as scaled versions of their single-photon counterparts when the offset in frequency for the xy-pulse is set to meet the two-photon resonance conditions. In phantoms, for example, it has been shown that if a standard pulse sequence is provided and all of the transmit frequencies are shifted outside of the field of view and an extra z-axis RF at a frequency equal to that transmit frequency shift is applied, the resulting image will look almost identical to what is normally produced with single-photon schemes, when the flip angle is calibrated.

With an extra RF coil, standard slice-selective pulse sequences can be realized with all standard excitations replaced by multiphoton excitations. Also, in the case of no extra hardware, extra photons can be provided by oscillating the gradient fields.

In the case of oscillating gradients, the multiphoton interpretation provides the opportunity for the development and use of novel excitation pulse design techniques. The multiphoton interpretation of oscillating gradients allows the transformation of a standard slice selective adiabatic inversion pulse into a multiband one without modifying the RF pulse itself. The addition of oscillating gradients creates multiphoton resonances at multiple spatial locations and allows for adiabatic inversions at each location. Another example is the creation of a multiband multiphoton adiabatic inversion pulse using only a standard hyperbolic secant adiabatic pulse on the RF side. Such a pulse may be useful for simultaneous multi-slice imaging techniques.

Accordingly, the multiphoton framework and interpretation presents new flexibilities for imaging. Excitation need not be bound to the Larmor frequency, which opens doors to RF pulse design beyond the usual filter design and the potential for further imaging innovations. Within this framework, it becomes clear that these multiphoton excitations excite extra resonances, and concepts such as the Bloch-Siegert (BS) shift and adiabatic RF pulses readily generalize. The image space multiphoton excitation framework could also be used instead of k-space excitations to provide a more general 3D selective excitation.

According to one aspect of the technology, a multiphoton magnetic resonance imaging system is provided with at least one additional RF Coil configured to apply one or more fields along a z-axis, parallel to a main magnetic field $B_0$ of a conventional magnetic resonance imager.

Another aspect of the technology is a multiphoton MRI system configured to produce multiple magnetic field frequencies that excite multiphoton resonances to generate a signal for MRI while none of the frequencies is near the Larmor frequency.

Another aspect of the technology is a multiphoton MRI system configured to apply standard excitation pulses to a target with an RF field ($B_1$) polarized in the xy-plane, perpendicular to the main magnetic field $B_0$ while simultaneously oscillating gradients along a z-axis, parallel to the main magnetic $B_0$ field.

A further aspect of the technology is to provide a method comprising transforming a standard slice selective adiabatic inversion RF pulse into a multiband one without modifying the RF pulse itself.

Another aspect of the technology is to provide a platform for RF pulse design that is not bound to the Larmor frequency.

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWINGS

The technology described herein will be more fully understood by reference to the following drawings which are for illustrative purposes only.

DETAILED DESCRIPTION

Referring more specifically to the drawings, for illustrative purposes, systems and methods for magnetic resonance imaging with multiphoton excitation with a phase-modulated rotating frame are generally shown. The apparatus is based on a conventional MRI scanner architecture with a second RF coil that produces an RF field, parallel to the $B_0$ field or by oscillating the gradient fields. Several embodiments of the technology are described generally in FIG. 1A to FIG. 7 to illustrate the characteristics and functionality of the devices, systems and methods. It will be appreciated that the methods may vary as to the specific steps and sequence and the systems and apparatus may vary as to structural details without departing from the basic concepts as disclosed herein. The method steps are merely exemplary of the order that these steps may occur. The steps may occur in any order that is desired, such that it still performs the goals of the claimed technology.

Figure 1:
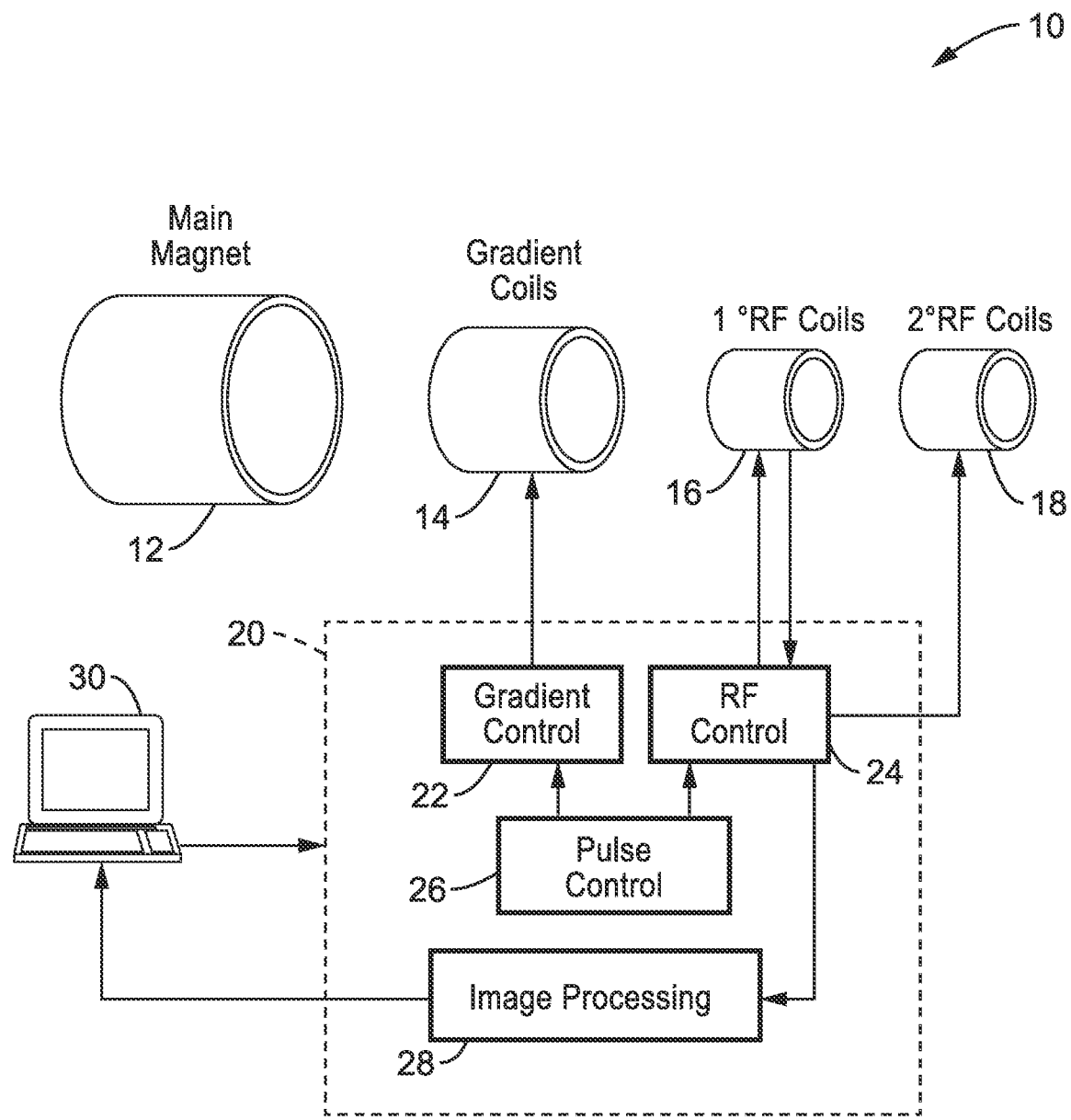
FIG. 1 is a schematic system diagram generally depicting a conventional magnetic resonance imaging system with a secondary ($B_{1,z}$) RF Coil configured to apply one or more magnetic fields along a z-axis according to one embodiment of the technology.

Turning now to FIG. 1, an embodiment of the apparatus 10 for multiphoton magnetic resonance imaging is shown schematically. In this embodiment, the MRI scanner apparatus 10 is expanded out to show the components that are normally nested to form a composite structure. The apparatus shown has a main magnet 12 and x, y and z gradient coils 14 in the conventional orientation. There is a set of primary RF Coils 16 and a secondary set of RF coils 18. The secondary $B_{1,z}$ solenoid 18 is aligned with $B_0$ in the system. Although secondary coil is illustrated in FIG. 1, additional secondary z-RF coils may be used.

The apparatus MRI scanner 10 also has a controller 20 with processor and programming subsystems and image processing. The gradient coils are generally controlled with a gradient control subsystem 22. The primary RF coils 16 and secondary RF coils 18 are generally controlled by the RF control subsystem 24. The gradient control 22 and RF control 24 subsystems are also controlled by the pulse control subsystem 26 that is programmed to control image acquisition using a variety of different pulse sequences and conditions. There is also an image processing subsystem 28 in this embodiment that is connected to a controller interface and display 30.

Figure 2:
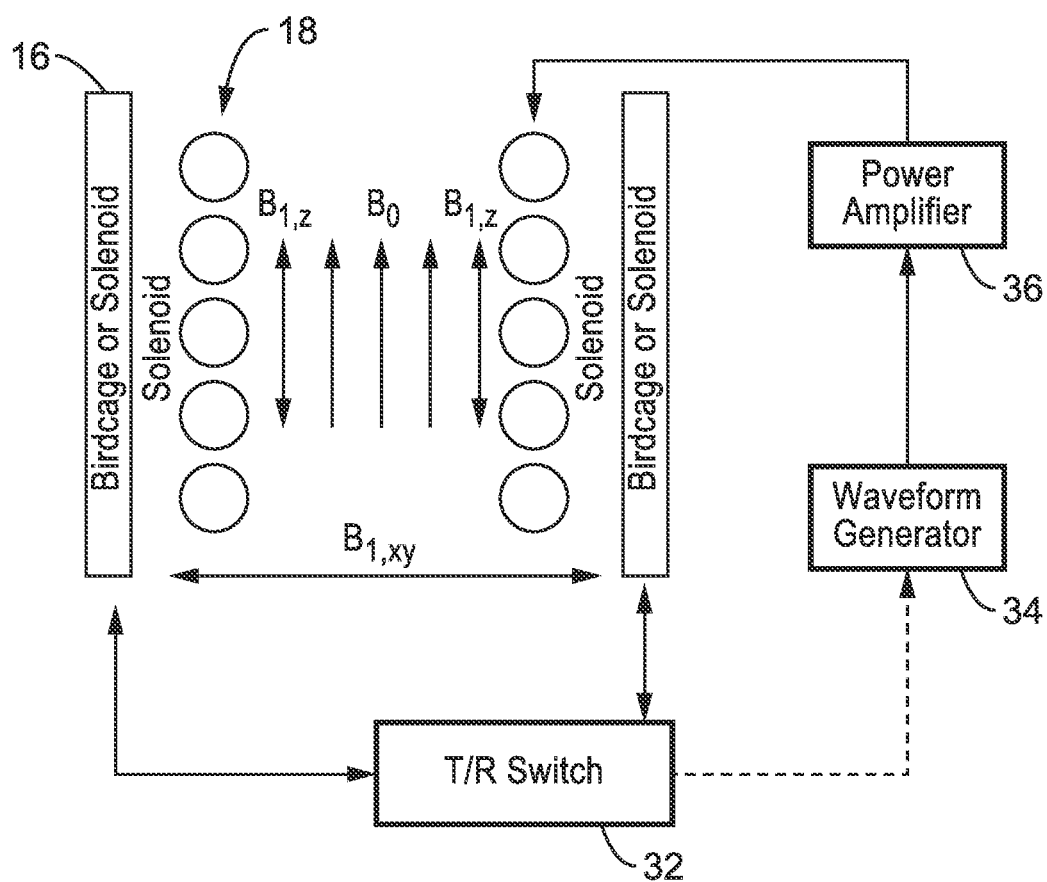
FIG. 2 is a schematic system diagram of a two-photon scanning setup with an extra ($B_{1,z}$) solenoid aligned with $B_0$. The control signal for the transmit/receive-switch (T/R switch) from the scanner triggers output from the waveform generator. The triggered signal is amplified and fed into the $B_{1,z}$ coil in this embodiment of the technology.

One preferred configuration of the primary and secondary RF coils in a two-photon scanning setup is detailed in FIG. 2. The control signal for the transmit/receive-switch (T/R switch) 32 from the scanner triggers an output from the waveform generator 3 of the pulse control 26 subsystem. The triggered signal is amplified by power amplifier 36 and fed into the secondary $B_{1,z}$ coil 18. The $B_{1,z}$ coil 18 may be driven directly from the amplifier 36, or the coil may be tuned and matched to a specific frequency range and then be driven from an amplifier 36. Tuning and matching may be necessary to achieve larger magnetic fields especially at higher frequencies. In one embodiment, the $B_{1,z}$ coil 18 is connected through a wire with cable traps to the power amplifier 36 with an optional tuning and matching network.

The main magnet 12 may be superconducting magnet or a permanent magnet depending on the type of scanner that is used. For a scanner with a superconducting magnet, the main magnet 12 is likely to be a solenoid structure with central bore with a $B_0$ field, and thus z-direction is parallel to the bore. In this case, to produce oscillating magnetic fields for multiphoton excitation, it is easiest to add another solenoid concentric to the main superconducting magnet and this ($B_{1,z}$ coil) is shown as the secondary RF Coil 18 in FIG. 1.

Figure 3A:
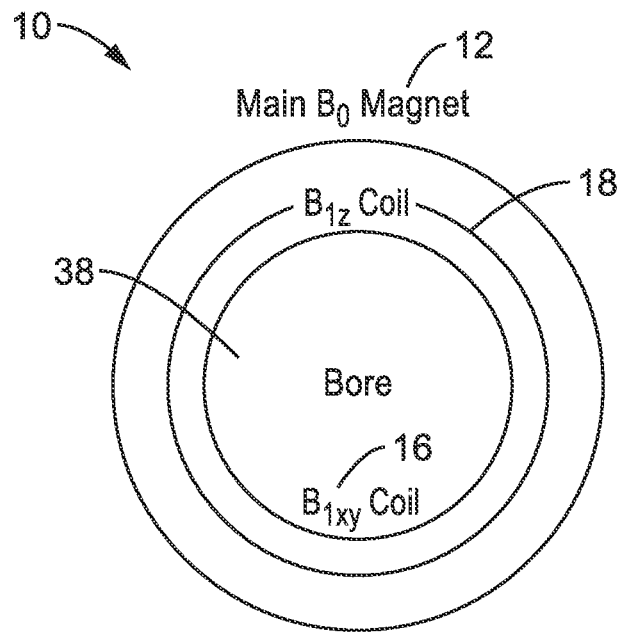
FIG. 3A is a schematic front view of a scanner with a superconducting solenoid magnet with a $B_0$ field and the z-direction is parallel to the central bore. All three coils are concentric to allow easy access to the bore of the magnet structure. The outermost coil is the superconducting coil for the magnet, the middle coil is the $B_{1,z}$ coil, and the innermost coil is the $B_{1,xy}$ or transverse RF coil. The $B_{1,z}$ and $B_{1,xy}$ coils may also exchange positions in this embodiment.

The secondary RF coil ($B_{1,z}$) coil 18 may fit inside or outside of the primary transverse RF coil ($B_{1,xy}$) 16 as shown in the front view of FIG. 3A. In this embodiment, all three coils are concentric to allow easy access to the bore 38 of the magnet structure. In FIG. 3A, the outermost coil is the superconducting coil 12 for the magnet, the middle coil is the $B_{1,z}$ coil 18, and the innermost coil is the $B_{1,xy}$ or transverse RF coil 16. It can be seen that the $B_{1,z}$ 18 and $B_{1,xy}$ 16 RF coils may exchange positions.

However, placing the transverse RF coil $B_{1,xy}$ 16 inside of the $B_{1,z}$ coil 18 is likely to lead to a higher signal to noise ratio (SNR) if the transverse coil $B_{1,xy}$ 16 is used for signal reception due to being physically closer to the object that is being imaged.

The construction of the second RF frequency $B_{1,z}$ coil 18 can be single layered or multi-layered, and the winding density may be dense or not. In choosing these parameters, one must take care to not wind the coil so densely that the high frequency transverse fields are shielded if any of these fields are to be transmitted or received outside of the $B_{1,z}$ coil, and the self-resonant frequency of the $B_{1,z}$ coil 18 should be above the maximum $B_{1,z}$ magnetic field frequency of interest. Denser coil windings, however, usually make the magnetic field of the $B_{1,z}$ coil 18 more uniform and may make achieving larger field strengths easier.

To reduce noise introduced into MR images by the addition of the $B_{1,z}$ coil 18, capacitors may optionally be added in parallel to the coil. Cable traps can also reduce noise and improve safety by reducing the coupling of Larmor frequency signals to the cable feeding the $B_{1,z}$ coil 18. The noise reduction capacitors may also be part of a tuning and matching network, which may be placed either inside or outside of the scanner room. The distance of the tuning and matching network to the coil usually inconsequential due to the typically very low frequencies and thus very long wavelengths used for the $B_{1,z}$ magnetic field.

Figure 3B:
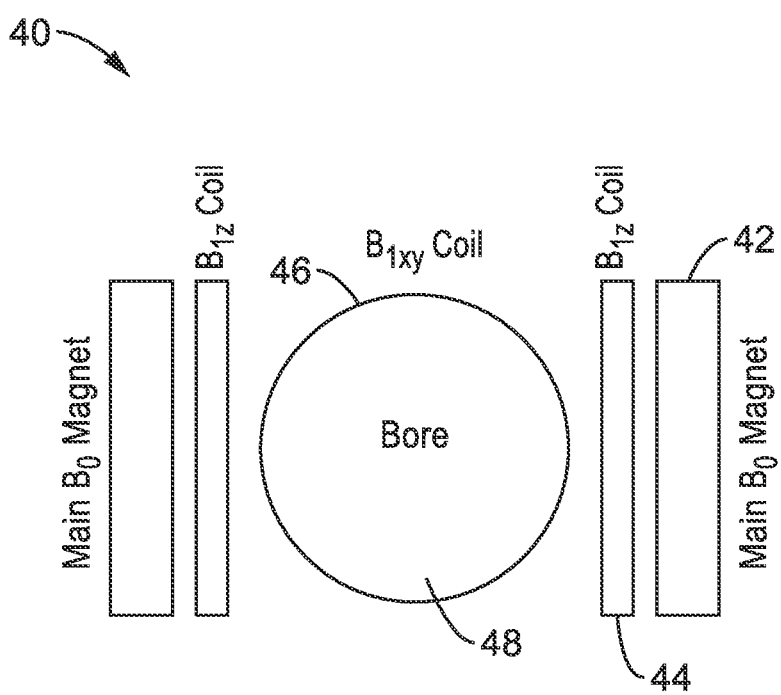
FIG. 3B is a schematic front view of an alternative scanner with a permanent magnet and $B_{1,z}$ coil is planar producing magnetic fields in the horizontal direction. The planar $B_{1,z}$ coil may be implemented as a circular, rectangular, or square spiral with the number and size of turns dependent on the desired electrical properties of the coil. The $B_{1,xy}$ coil produces fields into and out of the page. This arrangement allows access to the bore. The $B_{1,z}$ and $B_{1,xy}$ coils may exchange positions.

For an MRI scanner implemented using permanent magnets as seen in FIG. 3B, the $B_0$ field is likely to be perpendicular to the bore, in contrast to being parallel in the case of the superconducting solenoidal magnet embodiment shown in FIG. 3A. In the embodiment 40 of FIG. 3B, the permanent magnet 42 and RF frequency $B_{1,z}$ coil 44 produce magnetic fields in the horizontal direction. The $B_{1,xy}$ coil 46 produces fields into and out of the page. This arrangement allows access to the bore 46. In another embodiment, the $B_{1,z}$ coil 44 and the $B_{1,xy}$ coils 44 may exchange positions in the apparatus structure.

In the case of permanent magnets shown in FIG. 3B, the $B_{1,z}$ coils 48 can be implemented as planar coils instead of a solenoid shape in order to keep the bore 38 open and allow a sample or subject to be easily placed inside the magnet. The planar coil 44 may be implemented as a circular, rectangular, or square spiral with the number and size of turns dependent on the desired electrical properties of the coil.

The planar coil 44 may be implemented in many ways, but a printed circuit board (PCB) implementation is especially simple and preferred when high power is not required. The coil may be made multi-layer with the use of multiple PCB layers.

Two-photon excitation is used to generally illustrate the methods and apparatus characteristics. In this illustration, a fully geometric view of multiphoton excitation by taking a particular rotating frame transformation is presented. In this rotating frame, one observes that multiphoton excitations appear just like single-photon excitations again, and therefore, it is possible to readily generalize concepts already explored in standard single-photon excitation.

Standard single-photon excitation occurs when the RF field ($B_1$) is polarized in the xy-plane, perpendicular to the main magnetic field $B_0$. Multiphoton effects occur when one or more RF fields are added along the z-axis, parallel to the main magnetic field $B_0$. The term RF is used generally to include any oscillation frequency. It is also possible to have multiphoton effects with RF only in the xy-plane, however, the effects are usually orders of magnitude smaller.

Figure 4A:
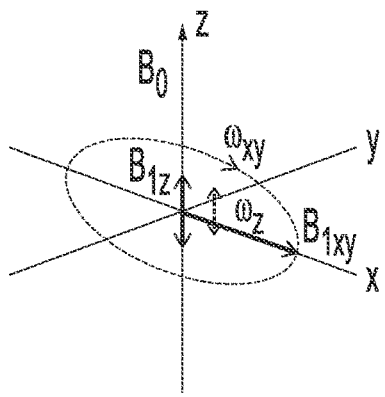
FIG. 4A is a diagram of the magnetic field setup in the laboratory frame with arbitrary frequencies for the xy- and z-RF fields according to the technology.
Figure 4B:
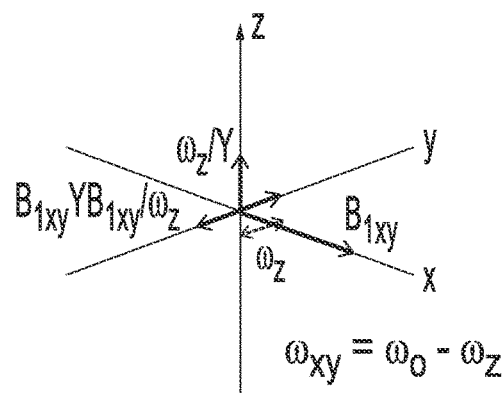
FIG. 4B is a diagram of the phase-modulated rotating frame with $\omega_{xy}=\gamma B_0-\omega_z$. There is a remaining static z-field that resonates with the oscillating field on the y-axis. In this case, both a xy- and z-photon are absorbed.
Figure 4C:
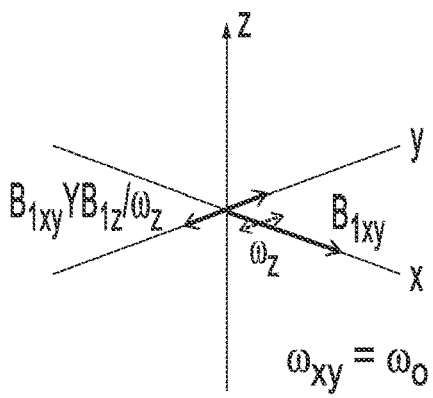
FIG. 4C is a diagram depicting the standard single-photon resonance. In the phase-modulated rotating frame with $\omega_{xy}=\gamma B_0$, there is no remaining static z-field, and the static x-field causes the resonance.
Figure 4D:
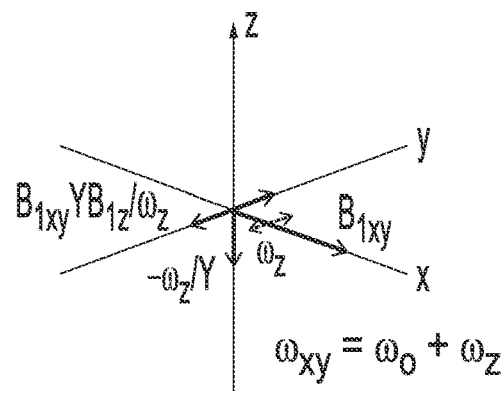
FIG. 4D is a diagram of the phase-modulated rotating frame with $\omega_{xy}=\gamma B_0+\omega_z$. There is a remaining static z-field that resonates with the oscillating field on the y-axis. In this case, a xy-photon is absorbed while a z-photon is emitted.

Single-photon and two-photon excitation conditions are shown in FIG. 4A through FIG. 4D. The magnetic field setup in the typical laboratory frame with arbitrary frequencies for the xy- and z-RF fields is shown in FIG. 4A. In the phase-modulated rotating frame with $\omega_{xy}=\gamma B_0-\omega_z$, there is a remaining static z-field that resonates with the oscillating field on the y-axis. In this case, both a xy- and z-photon are absorbed as illustrated in FIG. 4B. The standard single-photon resonance condition is shown in FIG. 4C. In the phase-modulated rotating frame with $\omega_{xy}=\gamma B_0$, there is no remaining static z-field, and the static x-field causes the resonance. In the phase-modulated rotating frame with $\omega_{xy}=\gamma B_0+\omega_z$, there is a remaining static z-field that resonates with the oscillating field on the y-axis. In this case, a xy-photon is absorbed while a z-photon is emitted as shown in FIG. 4D.

The phase-modulated rotating frame conditions shown in FIG. 4B through FIG. 4D are derived as follows. Consider two $B_1$ fields with frequencies $\omega_{xy}$ and $\omega_z$ along the xy-plane and z-axis respectively. The total magnetic field in the laboratory frame is $$B_z = B_0 + B_{1,z}\cos(\omega_z t) \tag{1}$$

$$B_x = B_{1,xy}\cos(\omega_{xy}t) \tag{2}$$

$$B_y = -B_{1,xy}\sin(\omega_{xy}t) \tag{3}$$

where the RF field in the xy-plane is clockwise circularly polarized; $B_{1,xy}$ and $B_{1,z}$ are amplitudes of each RF field. In a clockwise rotating frame with an angular velocity of $\omega_{rot}$, the effective $B_z$ field is $$B_{z,eff} = B_z - \frac{\omega_{rot}}{\gamma} \tag{4}$$

To generate time-invariant $B_{z,eff}$, we choose $$\omega_{rot} = \omega_{xy} + \gamma B_{1,z}\cos(\omega_z t) \tag{5}$$

This rotating frame is referred to as the phase-modulated rotating frame. This choice of $\omega_{rot}$ results in a non-stationary xy-plane RF field. To illustrate this effect, we examine the phase accrual of the xy-RF field in the rotating frame. Let $\theta$ be the phase, then $$B_{x,eff} = B_{1,xy}\cos(\theta) \tag{6}$$

$$B_{y,eff} = B_{1,xy}\sin(\theta) \tag{7}$$

By definition, $$\theta = \int_0^t (\omega_{rot} - \omega_{xy})dt = \frac{\gamma B_{1,z}}{\omega_z}\sin(\omega_z t). \tag{8}$$

The combination of Equations (4-8) gives:

$$B_{z,eff} = B_0 - \frac{\omega_{xy}}{\gamma} \tag{9}$$

$$B_{x,eff} = B_{1,xy}\cos\left(\frac{\gamma B_{1,z}}{\omega_z}\sin(\omega_z t)\right) \tag{10}$$

$$B_{y,eff} = B_{1,xy}\sin\left(\frac{\gamma B_{1,z}}{\omega_z}\sin(\omega_z t)\right) \tag{11}$$

Resonance conditions can be described when Equations (10) and (11) are Taylor expanded where $$\frac{\gamma B_{1,z}}{\omega_z} \ll 1$$

as $$B_{x,eff} \approx B_{1,xy} \tag{12}$$

$$B_{y,eff} \approx B_{1,xy}\frac{\gamma B_{1,z}}{\omega_z}\sin(\omega_z t) \tag{13}$$

It can be seen from Equations (9), (12) and (13), three potential resonances exist depending on the relative values of the frequencies as shown in FIG. 4B through FIG. 4D. The first is the single-photon resonance in the case where $\omega_{xy}=\gamma B_0$, when $B_{z,eff}=0$ and $B_{x,eff}$ tilts magnetization from the z-axis. This is the normal on-resonance condition as shown in FIG. 4C.

The second and third resonances are the two-photon resonances seen in FIG. 4B and FIG. 4D where $\omega_{xy}=\gamma B_0 \pm \omega_z$, and $B_{z,eff}=\mp\omega_z/\gamma$. The linearly polarized RF field $B_{y,eff}$ oscillates with an angular frequency of $\omega_z$, matching the amplitude of $B_{z,eff}$, which induces resonances. These two new resonances correspond to state transitions where a single xy-polarized photon is absorbed and a single z-polarized photon is absorbed or emitted, depending on whether the xy-frequency is below or above the Larmor frequency. From Equation (13), the effective angular nutation frequency for two-photon excitation is $$\omega_{nut} = \frac{\gamma B_{1,xy}\gamma B_{1,z}}{2\omega_z} \tag{14}$$

If more terms are kept in the Taylor expansion of Eqs. (10,11), higher-order excitations with three or more photons can be analyzed. However, Taylor expansion requires the condition $$\frac{\gamma B_{1,z}}{\omega_z} \ll 1.$$

Alternatively, one can exactly expand $B_{x,eff}$ and $B_{y,eff}$ using Bessel functions, which reveals that for any integer n, resonance occurs whenever $$\omega_{xy}=\gamma B_0+n\omega_z \tag{15}$$

and for each integer n, the corresponding effective angular nutation frequency is $$\omega_{nut} = \gamma B_{1,xy} J_n\left(\frac{\gamma B_{1,z}}{\omega_z}\right) \tag{16}$$

where $J_n$ represents the Bessel function of the first kind of order n. The n represents the number of z-axis photons in the resonance. As the maximum of Bessel functions occurs at gradually larger arguments for higher orders, larger $$\frac{\gamma B_{1,z}}{\omega_z}$$

is needed to generate muitiphoton resonances.

Generalizing further, in the case of photons of different frequencies along the z-axis, we simply multiply another Bessel function for that frequency. In the case of two different frequencies, there will be resonances whenever $$\omega_{xy}=\gamma B_0+n\omega_{z1}+m\omega_{z2} \tag{17}$$

and for each n and m, the corresponding angular nutation frequency is given by $$\omega_{nut} = \gamma B_{1,xy} J_n\left(\frac{\gamma B_{1,z1}}{\omega_{z1}}\right) J_m\left(\frac{\gamma B_{1,z2}}{\omega_{z2}}\right) \quad (18)$$

Additionally, off-resonance RF fields slightly shift resonance frequencies, a phenomenon termed the Bloch-Siegert shift. This shift also affects multiphoton excitation, as off-resonant RF fields are always employed. The resulting BS-shifts can be calculated based on all the off-resonant terms in the phase-modulated rotating frame. Specifically, each off-resonant term adds a BS-shift. To the second order, the BS-shift is $$\omega_{BS} = \frac{(\gamma B_{1,off})^2}{2\omega_{off}} \quad (19)$$

where $B_{1,off}$ is the magnitude of the off-resonant RF field and $\omega_{off}$ is the frequency offset from the resonance, which can be a single-photon resonance or any multiphoton resonance. In theory, the number of off-resonant terms, whose amplitudes are given by the integer orders of the Bessel function, will be infinite. The infinite sums can be approximated by the Carson's bandwidth rule, which heuristically states that approximately 98% of the power of a frequency-modulated signal will be contained in a bandwidth of $2(\beta+1)B$, where $\beta$ is the peak modulation index and B is the highest frequency in the modulating signal. In our case, $\beta$ is the largest $$\frac{\gamma B_{1,zn}}{\omega_{zn}}$$

and B is the largest $\omega_{zn}$.

In the case of one $B_{1,xy}$ and two $B_{1,z}$, where resonances occur at $\omega_{xy}=\gamma B_0 + k\omega_{z1} + l\omega_{z2}$, the off-resonant terms in the phase-modulated rotating frame are defined by:

$$B_{xy,off} = B_{1,xy} \sum_{(n,m)\neq(k,l)} J_n\left(\frac{\gamma B_{1,z1}}{\omega_{z1}}\right) J_m\left(\frac{\gamma B_{1,z2}}{\omega_{z2}}\right) e^{-i((k-n)\omega_{z1}+(l-m)\omega_{z2})} \quad (20)$$

Each of these terms contributes to the BS-shift as approximated by Equation (19), resulting in a total BS-shift of $$\omega_{BS\,total} = \frac{(\gamma B_{1,xy})^2}{2} \sum_{(n,m)\neq(k,l)} \frac{\left(J_n\left(\frac{\gamma B_{1,z1}}{\omega_{z1}}\right) J_m\left(\frac{\gamma B_{1,z2}}{\omega_{z2}}\right)\right)^2}{(k-n)\omega_{z1}+(l-m)\omega_{z2}} \quad (21)$$

The summation can be evaluated numerically with Carson's bandwidth rule.

Multiphoton excitation with a single xy-photon can be described with the following Bessel function. In the phase-modulated rotating frame, equations (9), (10) and (11) can be combined to form the relation $$B_{xy,eff} =$$

$$B_{1,xy}\cos\left(\frac{\gamma B_{1,z}}{\omega_z}\sin(\omega_z t)\right) + iB_{1,xy}\sin\left(\frac{\gamma B_{1,z}}{\omega_z}\sin(\omega_z t)\right) = B_{1,xy} e^{i\frac{\gamma B_{1,z}}{\omega_z}\sin(\omega_z t)}$$

with $J_n$ representing the Bessel function of the first kind with integer order n, the generating function of the Bessel function of the first kind is $$e^{\frac{x}{2}(z-z^{-1})} = \sum_{n=-\infty}^{\infty} J_n(x) z^n$$

When $z=e^{i\omega_z t}$, then $i\cdot\sin(\omega_z t)=\frac{1}{2}(z-z^{-1})$. Then the combined equation becomes:

$$B_{1,xy} e^{i\frac{\gamma B_{1,z}}{\omega_z}\sin(\omega_z t)} = B_{1,xy} e^{\frac{\gamma B_{1,z}}{2\omega_z}(z-z^{-1})} = B_{1,xy} \sum_{n=-\infty}^{\infty} J_n\left(\frac{\gamma B_{1,z}}{\omega_z}\right) e^{in\omega_z t} \quad (22)$$

Therefore, resonances occur whenever $$\omega_{xy} = \gamma B_0 + n\omega_z$$

and for each n, directly from the amplitude in the phase-modulated rotating frame, the effective angular nutation frequency is $$\omega_{nut} = \gamma B_{1,xy} J_n\left(\frac{\gamma B_{1,z}}{\omega_z}\right) \quad (23)$$

Alternatively, in the case of multiphoton excitation with one $B_{1,xy}$ and two $B_{1,z}$, fields, the Bessel functions are defined as follows. In this case, $B_z = B_0 + B_{1,z}\cos(\omega_{z1}t) + B_{1,z2}\cos(\omega_{z2}t)$ with a single $B_{1,xy}$ field. In the phase-modulated rotating frame, the effective fields are $$B_{z,eff} = B_0 - \frac{\omega_{xy}}{\gamma}$$

$$B_{x,eff} = B_{1,xy}\cos\left(\frac{\gamma B_{1,z1}}{\omega_{z1}}\sin(\omega_{z1}t) + \frac{\gamma B_{1,z2}}{\omega_{z2}}\sin(\omega_{z2}t)\right)$$

$$B_{y,eff} = B_{1,xy}\sin\left(\frac{\gamma B_{1,z1}}{\omega_{z1}}\sin(\omega_{z1}t) + \frac{\gamma B_{1,z2}}{\omega_{z2}}\sin(\omega_{z2}t)\right)$$

Where $$\alpha = \frac{\gamma B_{1,z1}}{\omega_{z1}} \text{ and } \frac{\gamma B_{1,z2}}{\omega_{z2}},$$

these equations can be rewritten as $$B_{xy,eff} = B_{1,xy} e^{i(\alpha\,\sin(\omega_{z1}t)+\beta\,\sin(\omega_{z2}t))} = B_{1,xy} e^{i\alpha\,\sin(\omega_{z1}t)} e^{i\beta\,\sin(\omega_{z2}t)}$$

Plugging Eq. (22) into this equation results in $$B_{xy,eff} = B_{1,xy} \sum_{n=-\infty}^{\infty} J_n(\alpha) e^{in\omega_{z1}t} \sum_{m=-\infty}^{\infty} J_m(\beta) e^{im\omega_{z2}t} \quad (24)$$

$$B_{xy,eff} = \sum_{n=-\infty}^{\infty} \sum_{m=-\infty}^{\infty} J_n(\alpha) J_m(\beta) e^{i(n\omega_{z1}t+m\omega_{z2}t)}$$

Equation (25) shows that in the phase-modulated rotating frame, xy-RF has angular frequencies of $n\omega_{z1}+m\omega_{z2}$. Thus, from Eqs. (23) and (25), resonances occur whenever $\omega_{xy}=\gamma B_0+n\omega_{z1}+m\omega_{z2}$, and the effective angular nutation frequency for n and m is $$\omega_{nut} = \gamma B_{1,xy} J_n\left(\frac{\gamma B_{1,z1}}{\omega_{z1}}\right) J_m\left(\frac{\gamma B_{1,z2}}{\omega_{z2}}\right) \quad (25)$$

For more than two frequencies along the z-axis, the analysis extends to having more multiplied Bessel functions, one for each new frequency involved.

The dynamics of nuclear magnetization under multiphoton excitation conditions can be described with an extension of the Bloch Equation that can be used to design general excitation pulses with single or multiple RF coils.

In the presence of multiple $B_1$ fields in x, y, and z directions, the Bloch Equation can be written as $$\begin{bmatrix} \dot{M}_x \\ \dot{M}_y \\ \dot{M}_z \end{bmatrix} = \gamma \begin{bmatrix} 0 & B_z(t) & -B_y(t) \\ -B_z(t) & 0 & B_x(t) \\ B_y(t) & -B_x(t) & 0 \end{bmatrix} \begin{bmatrix} M_x \\ M_y \\ M_z \end{bmatrix} + \begin{bmatrix} -\frac{M_x}{T_2} \\ -\frac{M_y}{T_2} \\ -\frac{M_z - M_0}{T_1} \end{bmatrix}. \quad (26)$$

In the rotating frame at rotating frequency of Larmor frequency ($\omega_0$), the B fields are, without loss of generality, $$B_z = B_{1,z}(r,t)\cos(\omega_{1,z}t), \quad (27)$$

$$B_x = B_{1,xy}(r,t)\cos((\omega_{1,xy}-\omega_0)t), \quad (28)$$

$$B_y = -B_{1,xy}(r,t)\sin((\omega_{1,xy}-\omega_0)t). \quad (29)$$

With a small-tip angle approximation, we can approximate $M_z(t) \approx M_0$. As a result, Eq. (26) becomes $$\begin{bmatrix} \dot{M}_x \\ \dot{M}_y \end{bmatrix} = \gamma \begin{bmatrix} 0 & B_z(t) \\ -B_z(t) & 0 \end{bmatrix} \begin{bmatrix} M_x \\ M_y \end{bmatrix} + \gamma \begin{bmatrix} -B_y(t)M_0 \\ B_x(t)M_0 \end{bmatrix}. \quad (30)$$

Define the transverse magnetization and magnetic field as $$m_{xy} = M_x + iM_y, \quad (31)$$

$$B_{1,xy} = B_x + iB_y \quad (32)$$

For pulsed $B_1$ fields over the time period from 0 to T, the solution to Eq. (5) which describes the transverse magnetization resulting from excitation, is given by $$m_{xy}(r,T) = i\gamma M_0 \int_0^T B_{1,xy}(r,t) e^{-i\gamma \int_t^T B_z(r,\tau)d\tau} dt \quad (33)$$

In general, the $B_1$ fields are spatially and temporally varying, e.g. when they are generated by surface coils. The spatial and temporal profiles provide the flexibility to design RF pulses that can optimize the excitation profiles.

In the following example, we assumed that the RF coils generate spatially uniform fields with the addition of gradient field.

$$B_z = B_{1,z}(t)\cos(\omega_{1,z}t) + G \cdot r \sin(\omega_{G,z}t), \quad (34)$$

$$B_x = B_{1,\rho}(t)\cos((\omega_{1,xy}-\omega_{rot})t), \quad (35)$$

$$B_y = -B_{1,\rho}(t)\sin((\omega_{1,xy}-\omega_{rot})t), \quad (36)$$

$$B_{1,xy} = B_{1,\rho}(t)e^{-i(\omega_{1,xy}-\omega_{rot})t} \quad (37)$$

Under these conditions, Eq. (8) becomes $$m_{xy}(r,T) = i\gamma M_0 \int_0^T B_{1,\rho}(t) e^{-i(\omega_{1,xy}-\omega_{rot})t} e^{-i\gamma \int_t^T B_{1,z}(\tau)\cos(\omega_{1,z}\tau)d\tau} e^{-i\gamma \int_t^T G \cdot r \sin(\omega_{G,z}\tau)d\tau} dt \quad (38)$$

In the Larmor-frequency rotating frame, i.e. $\omega_{rot}=\gamma B_0$, under the condition of multiphoton excitation, $\omega_{rot}-\omega_{1,xy}=n\omega_{1,z}$, Eq. (38) can be rewritten as $$m_{xy}(r,T) = i\gamma M_0 \int_0^T B_{1,\rho}(t) e^{in\omega_{1,z}t} e^{-i\gamma \int_t^T B_{1,z}(\tau)\cos(\omega_{1,z}\tau)d\tau} e^{-i\gamma k \cdot r} dt \quad (39)$$

With respect to multiphoton selective excitation, Eq. (39) provides a means to design RF pulses to achieve a desired excitation profile. In one approach, one can preselect $\omega_{1,xy}$, $\omega_{1,z}$ and T, then optimize the waveforms of $B_{1,\rho}(t)$, $B_{1,z}(t)$ and G(t) to achieve the desired excitation.

In the case of slice-selective excitation, where $B_{1,z}(t)$ is time invariant, i.e. it is a hard pulse, the integral involving $B_{1,z}(t)$ in Eq. (39) can be evaluated analytically as follows, $$m_{xy}(r,T) = i\gamma M_0 \int_0^T B_{1,\rho}(t) e^{in\omega_{1,z}t} e^{-i\frac{\gamma B_{1,z}}{\omega_{1,z}}(\sin(\omega_{1,z}T)-\sin(\omega_{1,z}t))} e^{-i\gamma k \cdot r} dt. \quad (40)$$

$$m_{xy}(r,T) = i\gamma M_0 e^{-i\frac{\gamma B_{1,z}}{\omega_{1,z}}\sin(\omega_{1,z}T)} \int_0^T B_{1,\rho}(t) e^{in\omega_{1,z}t} e^{i\frac{\gamma B_{1,z}}{\omega_{1,z}}\sin(\omega_{1,z}t)} e^{-i\gamma k \cdot r} dt. \quad (41)$$

Using the Bessel function expansion shown below $$e^{i\frac{\gamma B_{1,z}}{\omega_{1,z}}\sin(\omega_{1,z}t)} = \sum_{m=-\infty}^{\infty} J_m\left(\frac{\gamma B_{1,z}}{\omega_{1,z}}\right) e^{im\omega_{1,z}t}, \quad (42)$$

Eq. (41) can be rewritten as $$m_{xy}(r,T) = i\gamma M_0 e^{-i\frac{\gamma B_{1,z}}{\omega_{1,z}}\sin(\omega_{1,z}T)} \quad (43)$$

$$\int_0^T B_{1,\rho}(t) e^{in\omega_{1,z}t} \left(\sum_{m=-\infty}^{\infty} J_m\left(\frac{\gamma B_{1,z}}{\omega_{1,z}}\right) e^{im\omega_{1,z}t}\right) e^{-i\gamma k \cdot r} dt.$$

For a given n, i.e. n-photon excitation, the integral in Eq. (43) is only significant for term involving m=−n. With this knowledge, Eq. (43) can be simplified as, $$m_{xy}(r,T) = i\gamma M_0 e^{-i\frac{\gamma B_{1,z}}{\omega_{1,z}}\sin(\omega_{1,z}T)} J_{-n}\left(\frac{\gamma B_{1,z}}{\omega_{1,z}}\right) \int_0^T B_{1,\rho}(t) e^{-i\gamma k \cdot r} dt. \quad (44)$$

Eq. (44) shows that, if $B_{1,z}$ is a hard pulse, it only affects the phase and amplitude of the excitation. The slice profile and selection are determined by the pulse shape of $B_{1,xy}$.

Slice selection can also be achieved by shifting the frequency of $B_{1,z}$. For example, if we replace $\omega_{1,z}$ with a new frequency of $\omega_{1,z}+\Delta\omega$, Eq. (44) becomes $$m_{xy}(r, T) = i\gamma M_0 e^{-i\frac{\gamma B_{1,z}}{\omega_{1,z}}sin(\omega_{1,z}T)} J_{-n}\left(\frac{\gamma B_{1,z}}{\omega_{1,z} + \Delta\omega}\right) \int_0^T B_{1,\rho}(t)e^{-i\Delta\omega t}e^{-i\gamma k \cdot r} dt. \quad (45)$$

The slice excitation location is determined by the frequency shift of $\Delta\omega$ and the amplitude of the gradients. If the pulse duration is chosen such at $\omega_{1,z}T=n\omega$, Eq. (45) can be further simplified to $$m_{xy}(r, T) = i\gamma M_0 J_{-n}\left(\frac{\gamma B_{1,z}}{\omega_{1,z} + \Delta\omega}\right) \int_0^T B_{1,\rho}(t)e^{-i\Delta\omega t}e^{-i\gamma k \cdot r} dt. \quad (46)$$

The mathematical framework can also be adapted to simultaneous multi-slice excitation. In conventional single-photon excitation, multiple slices can be excited simultaneously by modulating the $B_{1,xy}$ field, e.g. by a trigonometric function. However, this increases the RF power and SAR deposition. With multiphoton excitation, it is possible to shift the modulation to the $B_{1,z}$ field. As the $B_{1,z}$ field has orders of magnitude lower frequency, the resulting SAR increase is negligible.

For example, the z-axis field can be designed as $$B_z(t) = B_{1,z}(a \cos(\omega_{1,z}t) + b \sin(\Delta\omega t)), \quad (47)$$

With $\Delta\omega \ll \omega_{1,z}$. Under this field, following the procedures above, the solution to the Bloch equation is $$m_{xy}(r, T) = i\gamma M_0 \int_0^T B_{1,\rho}(t)e^{in\omega_{1,z}t}\left(\sum_{m=-\infty}^{\infty} J_m\left(\frac{\gamma a B_{1,z}}{\omega_{1,z}}\right)e^{im\omega_{1,z}t}\right) \quad (48)$$

$$\left(\sum_{p=-\infty}^{\infty} J_p\left(\frac{\gamma b B_{1,z}}{\Delta\omega}\right)e^{ip\Delta\omega t}\right)e^{-i\gamma k \cdot r} dt.$$

Note, Eq. (48) also assumes $\omega_{1,z}T=n\pi$ for simplicity. Because, in general, $\Delta\omega \ll \omega_{1,z}$, the integral in Eq. (48) is only significant for $m=-n$, while all other terms cancel out due to the rapid oscillation of $\omega_{1,z}$. Eq. (48) further simplifies to $$m_{xy}(r, T) = \quad (49)$$
$$i\gamma M_0 J_{-n}\left(\frac{\gamma a B_{1,z}}{\omega_{1,z}}\right)\int_0^T B_{1,\rho}(t)\left(\sum_{p=-\infty}^{\infty} J_p\left(\frac{\gamma b B_{1,z}}{\Delta\omega}\right)e^{ip\Delta\omega t}\right)e^{-i\gamma k \cdot r} dt.$$

By proper choices of parameters, we can produce targeted excitation of multiple slices simultaneously.

Finally, Eq. (26) and (39) can be used to formulate a phasor description of consecutive nutation. Such a formulae can then be used to extend the SLR algorithm to multiphoton excitation.

Accordingly, a general approach for analyzing and implementing multiphoton MRI under a classical framework is described that unifies single-photon and multiphoton excitation under the same mathematical framework. The multiphoton interpretation predicts a type of excitation that occurs even when the RF field has no frequency components near the Larmor frequency. With the multiphoton interpretation, true-resonance conditions are established, and with this knowledge, intuition for nonlinear effects such as the Bloch-Siegert shift and adiabatic pulses follow.

Because multiphoton excitation applies RF fields with frequencies significantly shifted from the Larmor frequency, one compelling application of multiphoton MRI is simultaneous transmission and reception via frequency isolation. Simultaneous transmit and receive events provides the advantage of high imaging efficiency without dead time and high signal-to-noise ratio with minimal $T_2$ and $T_2^*$ decay and are especially useful for imaging short-$T_2$ species.

However, such a scheme may be most practical at low main magnetic field strengths because the efficiency of multiphoton excitation depends on an absolute, not relative, offset from the Larmor frequency. A simultaneous transmit and receive scheme may also require filters to separate the transmit frequency from the received frequency. Separating a 100 kHz and 50 kHz transmit and receive, for example, would be much easier than separating a 100.1 MHz and 100.05 MHz transmit and receive signals. Furthermore, at low fields, specific absorption rate (SAR) from the decreased excitation efficiency is a smaller concern, and larger RF fields are easier to produce at lower frequencies.

Multiphoton excitation in this framework also provides a new way to manipulate multiple RF waveforms and sample various interaction time scales. For example, a $B_{(1,z)}$ field could be chosen to be in sync with biological or chemical processes of interest and impact the corresponding MRI signal. The choice of multiphoton excitation RF frequencies could also alter the effect of magnetization transfer and chemical-exchange saturation transfer. In addition, multiphoton excitation pulses can alter signal evolution during excitation since post multiphoton excitation evolves similarly to single-photon excitation. For example, excitation RF is known to affect relaxation rates such as with $T_{1\rho}$.

Finally, multiphoton MRI offers additional options for designing excitation pulses as well as adapting existing pulse schemes. As illustrated in the examples herein, a simple single-band adiabatic inversion pulse may be made multiband via a proper choice of gradient waveforms. In general, for slice-selective excitation, RF pulse design can be extended beyond the usual filter design. For more general 3D selective excitation, an image space multiphoton excitation framework could be used instead of k-space excitation. As gradient and traditional RF coils gain more channels and spatial-temporal flexibility, much more can be achieved using multiphoton MRI to encode spatial, spectral and temporal information.

Figure 6:
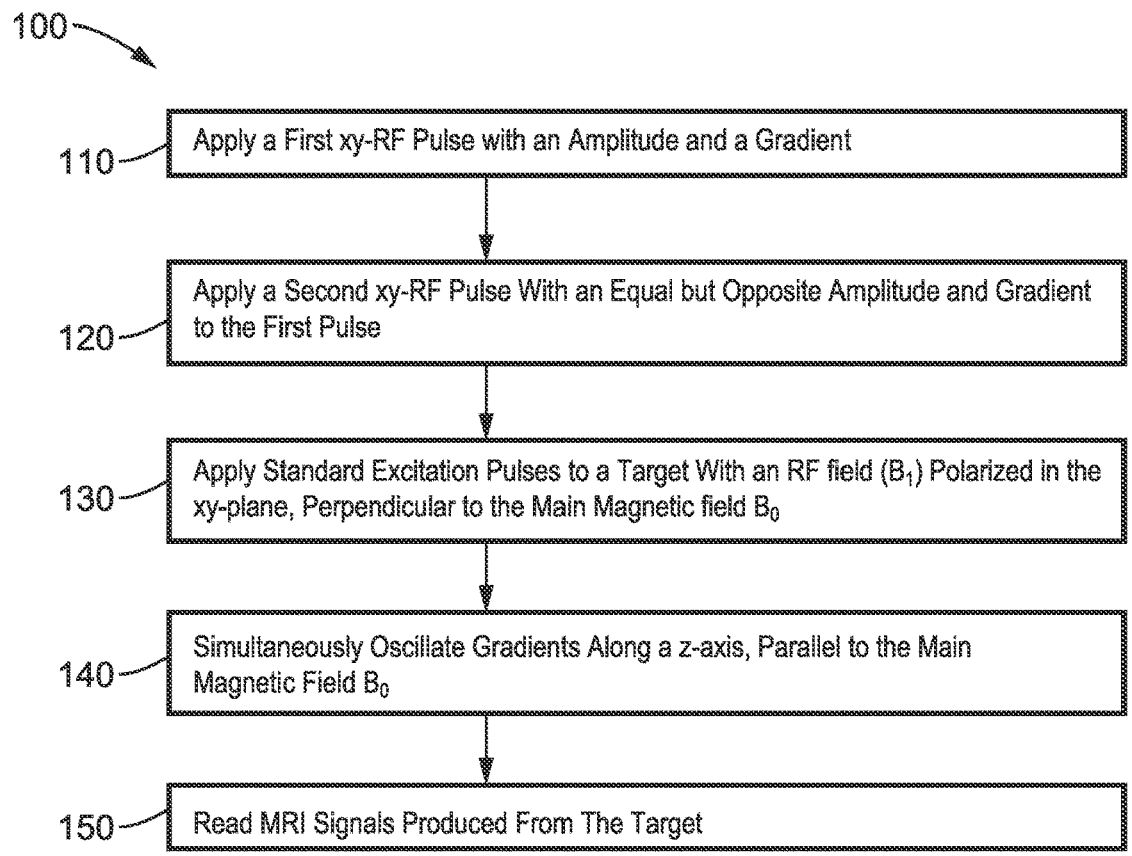
FIG. 6 is a functional block diagram of a method for multiphoton resonance imaging with magnetization preparation to cancel out the effects of single photon excitation but not the effective two-photon excitation according to one embodiment of the technology.

In one illustration of the methods, a diffusion MRI scheme 100 with magnetization preparation steps is shown schematically in FIG. 6 and demonstrated in Example 5. At block 110, a first xy-RF pulse is applied to a target that preferably has a positive amplitude and positive gradient. A second xy-RF pulse is applied to a target that preferably has an equal but negative amplitude and negative gradient from the first pulse at block 120. In one embodiment, the polarities of the pulses are switched. The effects of single photon excitation, but not the effective two-photon excitation, can be canceled out by performing the two xy-RF pulses.

After these magnetization preparation steps, the target is imaged with one of a variety of standard excitation pulses at block 130. In the embodiment shown in in FIG. 6, gradients along the z-axis are oscillated simultaneously with the excitation pulses at block 130. The MRI signals produced from the target are then read at block 150.

It can be seen that two-photon diffusion MRI offers a number of advantages and applications. For example, two-photon diffusion MRI can be tuned to probe certain frequency components of the diffusion process that is indicative of tissue property including cell density, geometry and disease-related lesions. In addition, two-photon diffusion MRI is immune to bulk motion in contrast to conventional pulsed-gradient spin echo diffusion. As a result, two-photon diffusion MRI can allow high spatial resolution scans.

Figure 7:
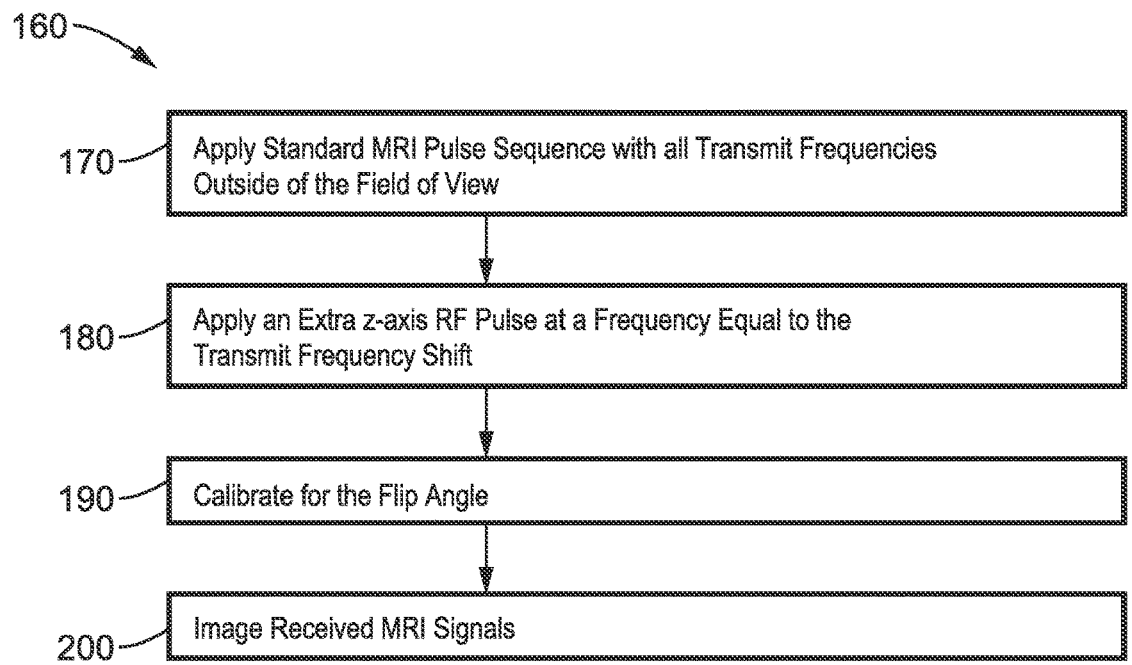
FIG. 7 is a functional block diagram of a method for multiphoton resonance imaging according to another embodiment of the technology.

In the embodiment illustrated in FIG. 7 and demonstrated in Example 6, the multiphoton imaging scheme 160 is adapted for typical in vivo MRI imaging. At block 170, a standard MRI pulse sequence is applied with transmit frequencies outside of the field of view. One or more z-RF pulses are applied at a frequency equal to the transmit frequency shift at block 180. The flip angle can be calibrated at block 190 and the resulting MRI signals received and imaged at block 200. For the two-photon case, the flip angle is proportional to $B_{1,xy}$ multiplied by $B_{1,z}$.

As illustrated in Example 6, in vivo imaging can be achieved using multiphoton excitation and has comparable signal to noise ratios to single-photon excitation when similar sequences are used without single-photon excitations.

The technology described herein may be better understood with reference to the accompanying examples, which are intended for purposes of illustration only and should not be construed as in any sense limiting the scope of the technology described herein as defined in the claims appended hereto.

Example 1

To demonstrate the multiphoton MRI concepts, numerical simulations were performed to verify the analytical framework of the system. Bloch simulations, resonance verification and nutation frequency verification simulations were performed.

Bloch simulations were performed in Matlab R2017a (MathWorks, Inc., Natick, MA) using the built-in ode45 or ode113 solver. All xy-frequencies represented offsets from the Larmor frequency, as a rotating frame at the Larmor frequency was used.

Multiphoton resonances were verified by evaluating resulting transverse magnetization versus various combinations of xy- and z-RF frequencies (10-ms hard pulses). RF pulses in xy and z were swept from −30 kHz to 30 kHz and from 0 to 30 kHz with a step size of 60 and 30 Hz, respectively. For each simulated point, $B_{1,z}$ was chosen such that $$\frac{\gamma B_{1,z}}{\omega_z} = 1.$$

$B_{1,xy}$ was kept at a constant 1 µT.

The transverse magnetization generated by two perpendicular $B_1$ pulses ($B_{1,xy}$ and $B_{1,z}$) showed five lines of elevated intensity versus a 2D frequency sweep. The observed center brightest line, corresponding to $\Delta\omega_{xy}=0$, represented the single-photon resonance. The two lines closest to the center line represented the two-photon resonances, where $\Delta\omega_{xy}\approx\pm\omega_z$. The two furthest lines represent three-photon resonances, where $\Delta\omega_{xy}\approx\pm2\omega_z$. It should be noted that with the fixed ratio of $$\frac{\gamma B_{1,z}}{\omega_z} = 1,$$

the excitation efficiency decreases towards higher-order resonances. To further illustrate the multiphoton-resonance nature, time and frequency domain plots of a two-photon excitation were created where there is no component of the excitation at the Larmor frequency.

The nutation frequency simulation was compared with the analytical nutation frequency expressions over a wide range of magnetic field strengths and frequencies that may be encountered in practice. Because the analytical expressions give resonance nutation frequencies, the simulation considered the BS-shift as described above. For example, if a two-photon resonance is desired with $\omega_{xy}=\omega_0+1000$ rad/s and $\omega_z=10000$ rad/s, and it was predicted that the BS-shift was +87 rad/s for this resonance, then the xy-frequency was shifted by the BS-shift such that it hit the desired resonance. That is, for the simulation, the frequencies $\omega_{xy}=\omega_0+10087$ and $\omega_z=10000$ would be used instead. Analytical transverse magnetizations were also calculated using an effective flip angle obtained by multiplying the effective nutation frequency with the hard pulse duration of 10 ms.

Without a BS-shift compensation, there was significant deviation between Bloch simulation and transverse magnetization derived analytically from Eq. (16), especially at higher $B_{1,xy}$ strengths. However, with the pre-compensation, the simulation matches nearly exactly the results of the analytical expressions. The effective flip angle was also observed to increase linearly with the strength of $B_{1,xy}$, but nonlinearly with increasing $B_{1,z}$ and $\omega_z$, as $$J_1\left(\frac{\gamma B_{1,z}}{\omega_z}\right)$$

oscillates nonperiodically. Potential deviations between simulation and analytical expressions may occur when the BS-shift approximation is not accurate. The second-order BS-shift approximation that was used, however, works well for the range of values shown. While the amplitude of $B_{1,xy}$ has the strongest effect, all parameters influence the BS-shift.

Example 2

Preliminary scanner experiments were also performed to demonstrate the viability of the system. The MRI scanner experiments were performed on an Aspect 1T wrist scanner (Aspect Imaging, Shoham, Israel). Two-photon excitation with an extra z-RF coil and two-photon excitation with gradient coil oscillation were demonstrated.

Two-photon RF pulses were transmitted simultaneously with a commercial coil at 44.73 MHz (i.e. Larmor frequency plus 130 kHz) and a homebuilt solenoid coil at 130 kHz. The homebuilt coil, resonated and matched at 130 kHz, was inserted into the commercial coil, producing RF in the $B_0$ direction. The input to the 130-kHz coil was connected to a custom-built power amplifier (100 W, operational between 100 kHz to 1 MHz), which was connected to an arbitrary waveform generator (Keysight 33600A; gated burst mode and 130 kHz). The gating signal was synchronized to the scanner's control signal for the transmit/receive-switch, such that the 130 kHz signal was generated whenever the scanner transmitted a RF pulse. The 130 kHz shift was chosen as the shift is sufficiently large to avoid single-photon resonances. In other words, all the frequencies transmitted by the two coils were outside of the range of single-photon excitation within the field of view.

Gradient-echo images of a lemon were acquired with: TR/TE=500/3.0 ms, FA=10°, 500-μs sincgauss pulse, resolution=0.625×0.625×3 mm$^3$, 80×80 mm$^2$ FOV, 10 slices, 40-kHz readout bandwidth, axial orientation, 66-sec scan time.

Gradient-echo images of a country-style pork rib were acquired with: TR/TE=500/8.4 ms, FA=45°, 10-ms sincgauss pulse, resolution=0.625×0.625×2 mm$^3$, 80×80 mm$^2$ FOV, 10 slices, 40-kHz readout bandwidth, coronal orientation, 66-second scan time.

With a standard gradient-echo sequence, the two-photon resonance was shown to produce similar image quality as those of the single-photon resonance for both lemon and pork rib targets.

Two-photon excitation with gradient coils was also demonstrated. Oscillating gradients can also provide z-axis RF. For example, given a sinusoidal gradient vector $\vec{G} \sin(\omega_z t)$, the amplitude of the resulting z-axis RF is spatially linearly varying as $B_{1,z} = \vec{G} \cdot \vec{r} \sin(\omega_z t)$.

The corresponding flip angles were also spatially varying following the nutation frequency obtained with Eq. (16). As an illustration, a copper-sulfate-solution phantom was non-selectively excited using the x or y gradient oscillating at 16 kHz in conjunction with an xy-RF offset by −16 kHz from the Larmor frequency. A Larmor-frequency 180° pulse was used to only refocus the center slice. Other parameters were: TR/TE=500/8.4 ms, 700-μs excitation pulse (180° SLR RF pulse and 0.386 G/cm sinusoidal gradient), 700-μs 180° SLR refocusing pulse, resolution=0.625×0.625×5 mm$^3$, 80×80 mm$^2$ FOV, 2 slices, 40-kHz readout bandwidth, axial orientation, 66-second scan time.

When using gradients as a z-axis RF source, the frequency range was limited by the gradient slew rate, and the resulting RF field varied linearly in space. Different excitation patterns corresponding to different flip angles were generated with $G_x$ and $G_y$ gradient and observed. When the z-axis RF (i.e. oscillating $G_x$ and $G_y$) was turned off, no excitation occurs, demonstrating its two-photon nature. This two-photon excitation differs from spatial and spectral selective excitation that assumes RF transmitted and received both at the Larmor frequency and makes a small-tip approximation.

Example 3

Employing gradients for multiphoton excitation also opens an avenue for novel pulse designs. As an example, multiband multiphoton adiabatic inversion pulses were created by combining a standard hyperbolic secant adiabatic inversion pulse with an oscillating gradient, in contrast to previous approaches that add multiple pulses together or periodically switch RF on and off. To implement it on the 1T Aspect scanner, a vendor-supplied 20-ms hyperbolic secant adiabatic inversion pulse was executed in the presence of a gradient waveform in the readout direction. The resulting inversion bands were imaged with a standard spin echo sequence with an inversion recovery time of 20 ms. This allowed the observation of adiabatic inversion bands as dark bands in the readout direction of the phantom.

Three different gradient waveforms were compared. The first gradient was a constant 1.2858 G/cm pulse that generated a standard single adiabatic inversion band. The second gradient was the constant 1.2858 G/cm pulse superimposed with a sinusoidal gradient (amplitude 2.5716 G/cm, frequency 5475 Hz). This frequency was chosen to be the Larmor frequency offset at 1 cm from the origin of the gradient system. The sinusoidal gradient amplitude was chosen to be twice that of the constant gradient such that at 1 cm from the center was $$\frac{\gamma B_{1,z}}{\omega_z} = 2$$

and the two-photon resonance is the most efficient resonance compared to any other resonances considered.

For this gradient pulse, a single-photon adiabatic inversion at the center of the image and two-photon adiabatic inversions at ±1 cm from the center were expected. Finally, the third gradient was the same as the second, except that the frequency of the sinusoidal component of the gradient was halved to 2737.5 Hz. These conditions were expected to produce a single-photon adiabatic inversion at the center of the image, a two-photon adiabatic inversion at ±0.5 cm from the center, and a three-photon adiabatic inversion at ±1 cm from the center. For the spin-echo readout, TR/TE=500/15.3 ms, FA=90°, resolution=0.16×0.16×5 mm$^3$, 80×80 mm$^2$ FOV, 2 slices, 40-kHz readout bandwidth, axial orientation, with a 66-second scan time.

It was found that the one, three, and five adiabatic inversion bands in the readout direction in the image were created by single-photon, two-photon and three-photon excitations. Although as many as five bands were produced in this illustration, it is possible to create even more bands. As the Bessel function values became more dispersed with higher-order resonances, power efficiency for the adiabatic inversion decreased and the total RF power needed to be increased. Other frequencies in the rotating frame of the multiphoton resonance may also gain relative power and affect the success of the adiabatic pulse. The inversion was effective for relatively low-order multiphoton resonances shown in this illustration. A 1D simulation of the inversion profiles for a similar setup was also conducted.

Example 4

To further demonstrate the how a multiphoton interpretation of excitation can open new avenues for novel pulse design, several power-efficient multiband adiabatic inversion pulses were designed and tested. Such pulses may be useful for simultaneous multi-slice imaging techniques or other more exotic pulse sequences that make use of adiabatic pulses.

Multiphoton excitation occurs whenever the multiphoton resonance condition is satisfied where integer multiples of multiple RF frequencies sum to equal the Larmor frequency. One form of multiphoton excitation in MRI occurs with a single photon polarized in the xy-plane ($B_{1,xy}$ with frequency $\omega_{xy}$) and one or more photons polarized along the z-axis ($B_{1,z}$ with frequency $\omega_z$). Since the magnetic fields of gradient coils in MRI are oriented along the z-axis, by oscillating gradients, it is possible to provide z-axis photons for multiphoton resonances.

Furthermore, in the case of a single gradient frequency, the argument to the Bessel function will be the ratio of the AC gradient strength to the DC gradient strength multiplied by the order of the Bessel function. Thus, if the AC gradient strength is chosen to be 1.5 times the DC gradient strength, excitation bands will be produced corresponding to an unscaled $B_{1,xy}$ at the center for the single-photon resonance, plus/minus $J_1(1.5)$ scaling for two photon resonances, plus/minus $J_2(3.0)$ scaling for three photon resonances, etc., until it is outside of the field of view.

It can be seen that this example provides a good choice for the AC gradient strength, as the Bessel functions are nearly maximized. Although an adiabatic excitation is illustrated here, this scheme works for both adiabatic and non-adiabatic excitation.

In this illustration, multiphoton excitation occurs with one photon from a traditional RF source and one or more photons from oscillating gradients. By a proper choice of oscillating gradients, it is possible to meet the multiphoton resonance conditions at multiple spatial locations, and thus achieve multiband multiphoton adiabatic inversions. Only a slightly scaled standard adiabatic pulse was needed on the traditional RF side.

The methods and pulses were evaluated with simulations, phantoms and in vivo experiments on a 3T scanner. In the simulations, an 8 ms hyperbolic secant RF pulse with parameters $A_0=22$ µT, $\mu=4.29$, and $\beta=800$ rad/s was simulated with a) only a DC gradient, b) a DC gradient and a 5475 Hz gradient with 1.5 times the amplitude of the DC, and c) a DC gradient and a 2737.5 Hz gradient with 1.5 times the amplitude of the DC. One, three, and five adiabatic inversion bands respectively were present in the field of view.

Each simulated multiphoton multiband adiabatic inversion pulse was implemented in an inversion-recovery-prepared 2D fast spin echo sequence on a GE 3T MR750w scanner. The pulse sequence was coded using KSFoundation Epic. To view the multiband inversion profiles, the inversion-pulse gradients were created along an axis perpendicular to the fast spin echo imaging plane.

Waveform plots for multiphoton multiband adiabatic inversion pulse generated by KSFoundation Epic's sequence plotting. In this case, The DC gradient is 0.2 G/cm, the AC gradient was 1.5 times the DC gradient strength, and the hyperbolic secant RF pulse has nominal parameters $A_0=22$ µT, $\mu=4.9$, and $\beta=800$ rad/s. The pulse duration is 8 ms. The AC gradient frequency is 2737.5 Hz, which lead to a maximum gradient slew rate of 51.6 T/m/s, which was well within standard hardware capabilities.

Multiband adiabatic inversions were evaluated on a spherical phantom with various parameters. The first was an 8 ms pulse with a 0.1409 G/cm DC gradient, 2737.5 Hz AC gradient, and off-center positioning. The second was an 8 ms pulse with a larger 0.2 G/cm DC gradient and slightly larger 3 kHz AC gradient frequency. The third was 12 ms pulse with $\mu=4$, and $\beta=600$ rad/s and a larger 0.2 G/cm DC gradient and higher 5.5 kHz AC gradient frequency.

Finally, five band multiphoton multiband adiabatic inversion pulses were also applied to image the human brain in vivo with inversion recovery times of a) 400 ms, b) 650 ms, and c) 2500 ms. The white matter, gray matter and CSF could be seen to be selectively attenuated based on the inversion recovery time.

Accordingly, it is possible to design power-efficient multiband adiabatic inversion pulses using a multiphoton interpretation of excitation. Standard hyperbolic secant shaped pulses may be used for the RF and properly chosen oscillating gradients can create additional bands. This example demonstrates how a multiphoton interpretation of excitation can open new opportunities for pulse design.

Example 5

The incorporation of multiphoton excitation in diffusion MRI was illustrated with two-photo excitation. As indicated previously, the two-photon MRI scheme utilizes two RF fields: one in the xy-plane and one along the z-axis. Since gradient fields in MRI are oriented along the z-axis, oscillating the gradients can provide the extra photons needed for two-photon resonances. This, however, is not the only way to generate excitation using the gradients. If a constant gradient is used instead of an oscillating gradient, and the spins physically oscillate in space, then as the spins move back and forth along the constant gradient, they will experience an oscillating field along the z-axis. With this effective oscillating z-axis field, it is possible to again excite two-photon resonances, with the caveat that the z-axis photon is a false, virtual photon. The physical oscillation in space occurs naturally with diffusion in MRI. Thus, with two-photon concepts, it is possible to acquire a form of diffusion encoding in MRI.

Starting at thermal equilibrium, with the magnetization aligned with $B_0$, by applying an off-resonant xy-RF field and constant gradient, we become sensitive to diffusion oscillations at frequencies equal to the off-resonant frequency. This is because resonance conditions for excitation are met. However, because diffusion is random motion, the oscillations will have a random initial phase, and thus, within a voxel, excitation will be in random directions. The random directions cancel out producing a saturation effect. The total magnetization vector remains aligned with $B_0$, but its magnitude is reduced. To get a diffusion encoded image, standard pulse sequences can be used along with this magnetization preparation step.

In this case, it is desirable to only produce excitation from the effective two-photon resonance and not the usual single-photon resonance. Because the low frequency xy-RF offset is capable of generating coherent single-photon excitation, the sensitivity to low frequency diffusion oscillations can be impaired.

To get around this, two xy-RF pulses may be performed that will cancel out the effects of single photon excitation but not the effective two-photon excitation. The first xy-RF pulse should be played out with a positive amplitude and positive gradient. The second xy-RF pulse should be played out with an equal but negative amplitude and an equal but negative gradient to the first. The carrier frequencies should be shifted such that the same spatial positions are excited for each pulse. With this setup, the single-photon excitations cancel out as the amplitudes are opposite and the carrier frequencies are shifted so that the spins see two equal but antiparallel magnetic fields in the rotating frames of the RF frequencies. For the effective two-photon excitations, there are opposite amplitudes for the xy-RF as well as a negative effective z-field for the second pulse due to the reversed gradient. These two negatives cancel out, and the effective two-photon excitation remains.

Example 6

To further demonstrate the adaptability of the apparatus and methods, the multiphoton MRI apparatus and methods were used for in vivo imaging. In vivo imaging can be achieved using multiphoton excitation and has comparable signal to noise ratio (SNR) compared with single-photon excitation when similar sequences are used.

In this illustration, in vivo imaging with a multiphoton excitation technique was performed at 1T. To produce multiphoton excitation, a secondary RF coil was built that produces an RF field, parallel to the $B_0$ field. Designed for kHz frequencies, this coil consists of two layers of traces in a spiral configuration on a printed circuit board (PCB).

Adding this low-frequency coil to an Aspect 1T Wrist Scanner, it was possible to acquire gradient echo images with two-photon excitation of a human hand in vivo.

To achieve multiphoton excitation in an Aspect 1T wrist scanner (Aspect Imaging, Shoham, Israel), a vendor-provided solenoid RF coil was used with an additional homebuilt low-frequency spiral coil (see FIG. 3B) to produce the orthogonal RF fields $B_{1,xy}$ and $B_{1,z}$ respectively. By using two orthogonal fields with frequencies whose sum or difference equals the Larmor frequency, it was possible to produce two-photon excitation. The $B_{1,z}$ coil was powered by a waveform generator (Keysight 33600A) at 20 kHz to produce a secondary excitation field. No external power amplifier was required. In order to reduce noise, an extra 10 nF capacitor was connected in parallel with the spiral coil to produce a lowpass filter. The waveform generator was synchronized to the T/R switch of the scanner in order to turn off the low-frequency coil's signal during the receive period.

Figure 5A:
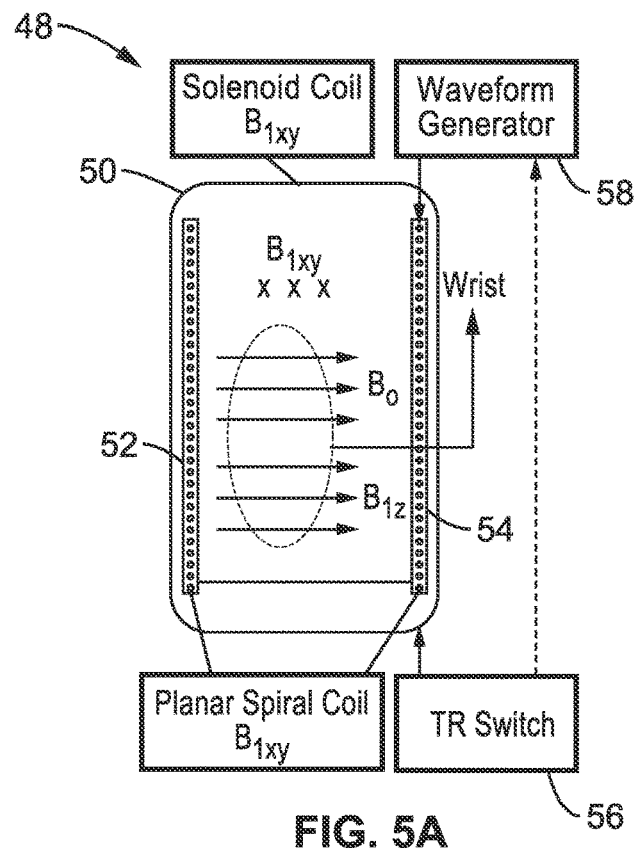
FIG. 5A is a schematic front view diagram of the wrist scanner set up with an additional pair of spiral coils for an extra $B_{1,z}$ field, where a hand would go into the page through the dotted oval.

For this illustration, a pair of planar custom spiral coils were built to generate the extra low-frequency $B_{1,z}$ field. The scanning set-up with an additional pair of spiral coils for an extra $B_{1,z}$ field is shown schematically in FIG. 5A and FIG. 5B. In FIG. 5A a front view of the wrist scanner set-up is shown schematically where a hand would go into the page through the dotted oval. This set-up is also shown generally in FIG. 3B. It can be seen in FIG. 5A and FIG. 5B that a pair of printed circuit boards with planar $B_{1,z}$ spiral coils 52, 54 are placed within a $B_{1,xy}$ solenoid coil 50. The system also had a transmit-receive (T/R) switch 56 and waveform generator 58 As shown schematically in FIG. 5A.

Figure 5B:
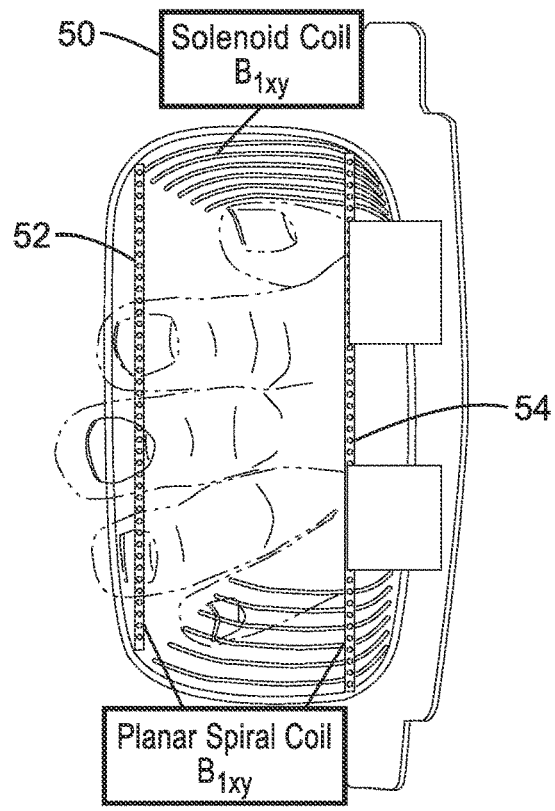
FIG. 5B is a back view diagram depicting the placement of a hand inserted into the bore of the scanner apparatus of FIG. 5A.

FIG. 5B depicts the back view of the physical structure with a hand in place within the bore. In this embodiment, the $B_{1,z}$ spiral coils 52, 54 were planar circular spirals. The planar structure was chosen due to the shape- and size-limitations of the solenoid T/R coil and the unique bore geometry of the Aspect scanner. Specifically, the $B_0$ field runs perpendicular to the bore of the scanner, so in order to keep the bore open, a standard solenoid could not be used to produce $B_{1,z}$ because it would block access to the bore. However, the pair of planar coils placed on each side of the hand allowed convenient access.

Each planar coil in this example had a dense spiral configuration to maximize the uniformity of the $B_{1,z}$ field with 68 turns and a 0.3 mm for trace width and a 0.2 mm spacing between traces. Each planar spiral coil was fabricated on a 2-layer standard printed circuit board (PCB) and the two layers had identical, but mirrored spirals with a via connection in the center. The mirroring was selected to ensure that the magnetic fields of the two layers would constructively add. The total DC resistance was 20.2 ohms. The large number of turns increases the power-efficiency for low-frequency magnetic field production. Because the coils are non-resonant coils designed for use at low frequencies, wavelength effects were not an issue, eliminating the need for tuning and matching.

To compare single-photon and two-photon images, images using single-photon excitation were first acquired by turning off $B_{1,z}$ waveform generator 58 using a standard 2D GRE pulse sequence known in the art. Imaging parameters are shown in Table 1. The $B_{1,z}$ waveform generator was then turned on to produce the additional source of photons and shifted the frequency of $B_{1,xy}$ accordingly. In order to transmit $B_{1,xy}$ at a frequency offset, the center slice position was set to be far outside of the field of view. The center slice position that produces 20 kHz offsets at a target location was calculated using the slice thickness and RF pulse bandwidth.

Images of the hand of a healthy volunteer were successfully obtained using both single- and two-photon excitation. The resulting images of both types of excitations have similar SNR with slight differences in contrast. The two-photon images had inhomogeneous intensity towards the edges of the FOV due to the inhomogeneous $B_{1,z}$ field generated by the pair of spiral coils that had reduced field strength towards the edge of the coils.

However, it was not possible to quantitatively compare image contrast due to the inhomogeneous $B_{1,z}$ field produced by the homebuilt spiral coil which generated spatially varying flip angles. It should be noted that the $B_{1,xy}$ flip Angle corresponds to only $B_{1,xy}$ power, not the result of the final two-photon flip angle. For the two-photon case, the flip angle is proportional to $B_{1,xy}$ multiplied by $B_{1,z}$.

To more accurately compare contrast, the spiral coil winding can be optimized to improve field homogeneity. In this case, specific absorption rate (SAR) was not an issue as the offset frequency was relatively low and thus, despite the decreased efficiency of multiphoton excitation, the $B_{1,xy}$ increase that was needed to achieve similar flip angles did not produce a significant SAR increase. If a larger offset frequency is desired, a greater $B_{1,z}$ will be required to achieve the same flip angle with the same $B_{1,xy}$. Since SAR is much less of a concern at lower frequencies, this should still be practical with larger power amplifiers for $B_{1,z}$.

From the description herein, it will be appreciated that the present disclosure encompasses multiple embodiments which include, but are not limited to, the following:

1. A multiphoton magnetic resonance imaging (MRI) system, the system comprising: (a) a magnetic resonance imager having a main magnet, gradient coils and at least one RF coil ($B_{1,xy}$) in a transverse plane; (b) at least one additional RF Coil ($B_{1,z}$) configured to apply one or more fields along a z-axis, parallel to a main magnetic field $B_0$ of the magnetic resonance imager; and (c) a controller operably coupled to the coils configured to generate multiple magnetic field frequencies that excite multiphoton resonances in a target to generate a signal for MRI imaging while none of the frequencies is near the Larmor frequency and to read generated MRI signals from the target.
2. The system of any preceding or following embodiment, wherein the main magnet is selected from the group consisting of a superconducting solenoid magnet and a permanent magnet.
3. The system of any preceding or following embodiment, wherein the main magnet, transverse RF coil ($B_{1,xy}$) and RF Coil ($B_{1,z}$) are concentric cylinders with a central axial bore, wherein the RF Coil ($B_{1,z}$) fits inside of the bore of the transverse RF coil ($B_{1,xy}$).
4. The system of any preceding or following embodiment, wherein the main magnet, transverse RF coil ($B_{1,xy}$) and RF Coil ($B_{1,z}$) are concentric cylinders with a central axial bore, wherein the transverse RF Coil ($B_{1,xy}$) fits inside of the bore of the RF coil ($B_{1,z}$).
5. The system of any preceding or following embodiment, wherein the at least one additional RF Coil ($B_{1,z}$), comprises: a first planar spiral with a spiral direction; and a second planar spiral with a spiral direction, the second spiral perpendicular to the first planar spiral and separated by a gap.
6. The system of any preceding or following embodiment, wherein the direction of the first spiral is opposite in direction to the spiral second planar spiral, wherein magnetic fields produced by the first and second spirals constructively add.

7. The system of any preceding or following embodiment, wherein the planar spirals are spirals selected from the group consisting of a square spiral, a rectangular spiral and a circular spiral.

8. The system of any preceding or following embodiment, wherein the transverse RF coil ($B_{1,xy}$) is positioned within the gap between the first and second planar spirals.

9. The system of any preceding or following embodiment, the controller further comprising: a waveform generator; a power amplifier connected to the waveform generator and to the at least one additional RF coil ($B_{1,z}$); and a transmit and receive switch operably connected to the transverse RF coil ($B_{1,xy}$) and the waveform generator.

10. The system of any preceding or following embodiment, wherein the connection between the power amplifier and the RF coil ($B_{1,z}$) further comprises a wire with cable traps and a tuning and matching network for noise reduction and increased magnetic field strength.

11. The system of any preceding or following embodiment, the controller further comprising: a processor and a non-transitory memory storing instructions executable by the processor; wherein the instructions, when executed by the processor, perform one or more steps comprising: transmitting multiphoton pulses simultaneously from the at least one RF coil and each additional RF coil to a target; and reading produced MRI signals from the target.

12. The apparatus of any preceding or following embodiment, wherein the instructions when executed by the computer processor further perform steps comprising: applying a first xy-RF pulse with a positive amplitude and a positive gradient; and applying a second xy-RF pulse with an equal but negative amplitude and a negative gradient to the first pulse; wherein single-photon excitations cancel out.

13. The apparatus of any preceding or following embodiment, wherein the instructions when executed by the computer processor further perform steps comprising: calibrating a flip angle; shifting transmit frequencies outside of a field of view with a standard pulse sequence; and applying an extra z-axis RF pulse at a frequency equal to that transmit frequency shift.

14. The apparatus of any preceding or following embodiment, wherein the multiphoton excitation comprises: producing photons polarized in the xy-plane ($B_{1,xy}$ with frequency $\omega_{xy}$); and producing photons polarized along the z-axis ($B_{1,z}$ with frequency $\omega_z$).

15. A method for multiphoton magnetic resonance imaging, the method comprising: (a) applying standard excitation pulses to a target with an RF field ($B_1$) polarized in the xy-plane, perpendicular to the main magnetic field $B_0$; (b) simultaneously oscillating gradients along a z-axis, parallel to the main magnetic field $B_0$; and (c) reading produced MRI signals from the target.

16. The method of any preceding or following embodiment, wherein the standard excitation pulse is selected from the group of pulses consisting of a hyperbolic secant pulse, a single band adiabatic inversion pulse, a single band excitation pulse and a sinc-Gauss pulse.

17. The method of any preceding or following embodiment, further comprising: applying a first xy-RF pulse with a positive amplitude and a positive gradient; and applying a second xy-RF pulse with an equal but negative amplitude and a negative gradient to the first pulse; wherein single-photon excitations cancel out.

18. The method of any preceding or following embodiment, further comprising: applying a first xy-RF pulse with a negative amplitude and a negative gradient; and applying a second xy-RF pulse with an equal but positive amplitude and a positive gradient to the first pulse; wherein single-photon excitations cancel out.

19. The method of any preceding or following embodiment, further comprising: transforming a standard slice selective adiabatic inversion RF pulse into a multiband one without modifying the xy-RF pulse.

20. A method for diffusion encoding in magnetic resonance imaging using multiphoton excitation, the method comprising: (a) using motion of spins in a gradient field as a source of z-axis photons; and (b) simultaneously transmitting off-resonant RF field ($B_1$) in an xy-plane, perpendicular to a main magnetic field $B_0$, to produce excitation.

21. The method of any preceding or following embodiment, further comprising: selecting values for $\omega_{1,xy}$, $\omega_{1,z}$ and T given the relation $m_{xy}(r,T) = i\gamma M_0 \int_0^T B_{1,\rho}(t) e^{in\omega_{1,z}t} e^{-i\gamma \int_t^T B_{1,z}(\tau) \cos(\omega_{1,z}\tau)d\tau} e^{-i\gamma k \cdot r} dt$; and optimizing waveforms $B_{1,\rho}(t)$, $B_{1,z}(t)$ and $G(t)$ to produce multiphoton selective excitation.

22. The method of any preceding or following embodiment, further comprising: providing a hard $B_{1,z}$ pulse; and determining slice profile by a pulse shape of $B_{1,xy}$.

23. The method of any preceding or following embodiment, further comprising: modulating the $B_{1,z}$ field for simultaneous multi-slice excitation.

24. A multiphoton magnetic resonance imaging (MRI) system, the system comprising: (a) a conventional magnetic resonance imager having at least one RF coil in a transverse plane; (b) at least one additional RF Coil configured to apply one or more fields along a z-axis, parallel to a main magnetic field $B_0$ of the conventional magnetic resonance imager; (c) multiple magnetic field frequencies that excite multiphoton resonances to generate a signal for MRI while none of the frequencies is near the Larmor frequency; and d) a processor and a non-transitory memory storing instructions executable by the processor; (e) wherein the instructions, when executed by the processor, perform one or more steps comprising: (i) transmitting multiphoton pulses simultaneously from the at least one RF coil and each additional RF coil to a target; and (ii) reading produced MRI signals from the target.

25. A method for multiphoton magnetic resonance imaging, the method comprising: (a) applying standard excitation pulses to a target with an RF field ($B_1$) polarized in the xy-plane, perpendicular to the main magnetic field $B_0$; (b) simultaneously oscillating gradients along a z-axis, parallel to the main magnetic field $B_0$; and (c) reading produced MRI signals from the target.

26. A method for multiphoton magnetic resonance imaging, the method comprising taking a particular rotating frame transformation of multiphoton excitation wherein multiphoton excitations appear as single-photon excitations.

27. A method for multiphoton magnetic resonance imaging, the method comprising using a low frequency coil, executing a standard slice selective RF pulse sequence with all of its excitations replaced with equivalent two-photon versions.

28. A method for multiphoton magnetic resonance imaging, the method comprising transforming a standard slice selective adiabatic inversion RF pulse into a multiband one without modifying the RF pulse itself.

29. A method for multiphoton magnetic resonance imaging, the method comprising designing RF and gradient pulses to achieve selective excitation by incorporating multiphoton excitation conditions in Bloch equations and excitation k-space.

30. A method for multiphoton magnetic resonance imaging, the method comprising designing RF and gradient pulses to achieve selective excitation by incorporating multiphoton excitation conditions in a Shinnar-Le Roux algorithm.

As used herein, the singular terms "a," "an," and "the" may include plural referents unless the context clearly dictates otherwise. Reference to an object in the singular is not intended to mean "one and only one" unless explicitly so stated, but rather "one or more."

As used herein, the term "set" refers to a collection of one or more objects. Thus, for example, a set of objects can include a single object or multiple objects.

As used herein, the terms "substantially" and "about" are used to describe and account for small variations. When used in conjunction with an event or circumstance, the terms can refer to instances in which the event or circumstance occurs precisely as well as instances in which the event or circumstance occurs to a close approximation. When used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, "substantially" aligned can refer to a range of angular variation of less than or equal to ±10°, such as less than or equal to ±5°, less than or equal to ±4°, less than or equal to ±3°, less than or equal to ±2°, less than or equal to ±1°, less than or equal to ±0.5°, less than or equal to ±0.1°, or less than or equal to ±0.05°.

Additionally, amounts, ratios, and other numerical values may sometimes be presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

All structural and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A multiphoton magnetic resonance imaging (MRI) system, the system comprising:
    (a) a magnetic resonance imager having a main magnet, gradient coils and at least one RF coil ($B_{1,xy}$) in a transverse plane;
    (b) at least one additional RF Coil ($B_{1,z}$) configured to apply one or more fields along a z-axis, parallel to a main magnetic field $B_0$ of said magnetic resonance imager; and
    (c) a controller operably coupled to said coils configured to generate multiple magnetic field frequencies that excite multiphoton resonances in a target to generate a signal for MRI imaging while none of the frequencies is near the Larmor frequency and to read generated MRI signals from the target.

2. The system of claim 1, wherein said main magnet is selected from the group consisting of a superconducting solenoid magnet and a permanent magnet.

3. The system of claim 1, wherein said main magnet, transverse RF coil ($B_{1,xy}$) and RF Coil ($B_{1,z}$) are concentric cylinders with a central axial bore, wherein said RF Coil ($B_{1,z}$) fits inside of the bore of the transverse RF coil ($B_{1,xy}$).

4. The system of claim 1, wherein said main magnet, transverse RF coil ($B_{1,xy}$) and RF Coil ($B_{1,z}$) are concentric cylinders with a central axial bore, wherein said transverse RF Coil ($B_{1,xy}$) fits inside of the bore of the RF coil ($B_{1,z}$).

5. The system of claim 1, wherein said at least one additional RF Coil ($B_{1,z}$), comprises:
    a first planar spiral with a spiral direction; and
    a second planar spiral with a spiral direction, said second spiral perpendicular to said first planar spiral and separated by a gap.

6. The system of claim 5, wherein said direction of said first spiral is opposite in direction to said spiral second planar spiral, wherein magnetic fields produced by the first and second spirals constructively add.

7. The system of claim 5, wherein said planar spirals are spirals selected from the group consisting of a square spiral, a rectangular spiral and a circular spiral.

8. The system of claim 5, wherein said transverse RF coil ($B_{1,xy}$) is positioned within said gap between the first and second planar spirals.

9. The system of claim 1, said controller further comprising:
    a waveform generator;
    a power amplifier connected to the waveform generator and to said at least one additional RF coil ($B_{1,z}$); and
    a transmit and receive switch operably connected to said transverse RF coil ($B_{1,xy}$) and said waveform generator.

10. The system of claim 9, wherein said connection between said power amplifier and said RF coil ($B_{1,z}$) further comprises a wire with cable traps and a tuning and matching network for noise reduction and increased magnetic field strength.

11. The system of claim 1, said controller further comprising:
    a processor and a non-transitory memory storing instructions executable by the processor;
    wherein said instructions, when executed by the processor, perform one or more steps comprising:

transmitting multiphoton pulses simultaneously from said at least one RF coil and each additional RF coil to a target; and
reading produced MRI signals from the target.

12. The apparatus of claim 11, wherein said instructions when executed by the computer processor further perform steps comprising:
applying a first xy-RF pulse with a positive amplitude and a positive gradient; and
applying a second xy-RF pulse with an equal but negative amplitude and a negative gradient to said first pulse;
wherein single-photon excitations cancel out.

13. The apparatus of claim 11, wherein said instructions when executed by the computer processor further perform steps comprising:
calibrating a flip angle;
shifting transmit frequencies outside of a field of view with a standard pulse sequence; and
applying an extra z-axis RF pulse at a frequency equal to that transmit frequency shift.

14. The apparatus of claim 11, wherein said multiphoton excitation comprises:
producing photons polarized in the xy-plane ($B_{1,xy}$ with frequency $\omega_{xy}$); and
producing photons polarized along the z-axis ($B_{1,z}$ with frequency $\omega_z$).

15. A method for multiphoton magnetic resonance imaging, the method comprising:
(a) applying standard excitation pulses to a target with an RF field ($B_1$) polarized in the xy-plane, perpendicular to the main magnetic field $B_0$;
(b) simultaneously oscillating gradients along a z-axis, parallel to the main magnetic field $B_0$; and
(c) reading produced MRI signals from the target.

16. The method of claim 15, wherein said standard excitation pulse is selected from the group of pulses consisting of a hyperbolic secant pulse, a single band adiabatic inversion pulse, a single band excitation pulse and a sinc-Gauss pulse.

17. The method of claim 15, further comprising:
applying a first xy-RF pulse with a positive amplitude and a positive gradient; and
applying a second xy-RF pulse with an equal but negative amplitude and a negative gradient to said first pulse;
wherein single-photon excitations cancel out.

18. The method of claim 15, further comprising:
applying a first xy-RF pulse with a negative amplitude and a negative gradient; and
applying a second xy-RF pulse with an equal but positive amplitude and a positive gradient to said first pulse;
wherein single-photon excitations cancel out.

19. The method of claim 15, further comprising:
transforming a standard slice selective adiabatic inversion RF pulse into a multiband one without modifying the xy-RF pulse.

20. A method for diffusion encoding in magnetic resonance imaging using multiphoton excitation, the method comprising:
(a) using motion of spins in a gradient field as a source of z-axis photons; and
(b) simultaneously transmitting off-resonant RF field ($B_1$) in an xy-plane, perpendicular to a main magnetic field $B_0$, to produce excitation.

21. The method of claim 20, further comprising:
selecting values for $\omega_{1,xy}$, $\omega_{1,z}$ and T given the relation $$m_{xy}(r,T) = i\gamma M_0 \int_0^T B_{1,\rho}(t) e^{in\omega_{1,z}t} e^{-i\gamma \int_t^T B_{1,z}(\tau)\cos(\omega_{1,z}\tau)d\tau} e^{-i\gamma k \cdot r} dt;$$ and optimizing waveforms $B_{1,\rho}(t)$, $B_{1,z}(t)$ and $G(t)$ to produce multiphoton selective excitation.

22. The method of claim 20, further comprising:
providing a hard $B_{1,z}$ pulse; and
determining slice profile by a pulse shape of $B_{1,xy}$.

23. The method of claim 20, further comprising modulating the $B_{1,z}$ field for simultaneous multi-slice excitation.

* * * * *